(12) United States Patent
McErlean et al.

(10) Patent No.: US 9,007,070 B2
(45) Date of Patent: Apr. 14, 2015

(54) MICROWAVE POWER MONITORING

(75) Inventors: Eamon McErlean, Alloa (GB); Gary Beale, Alloa (GB)

(73) Assignee: Emblation Limited, Alloa (GB)

( * ) Notice: Subject to any disclaimer, the term of this patent is extended or adjusted under 35 U.S.C. 154(b) by 160 days.

(21) Appl. No.: 13/509,835

(22) PCT Filed: Nov. 17, 2010

(86) PCT No.: PCT/GB2010/002114
§ 371 (c)(1),
(2), (4) Date: Jun. 15, 2012

(87) PCT Pub. No.: WO2011/061486
PCT Pub. Date: May 26, 2011

(65) Prior Publication Data
US 2012/0249165 A1    Oct. 4, 2012

Related U.S. Application Data

(60) Provisional application No. 61/262,206, filed on Nov. 18, 2009.

(51) Int. Cl.
*G01R 27/04*   (2006.01)
*A61B 18/18*   (2006.01)
*A61B 18/00*   (2006.01)

(52) U.S. Cl.
CPC ... *A61B 18/1815* (2013.01); *A61B 2018/00785* (2013.01)

(58) Field of Classification Search
USPC ............. 324/601, 638, 642; 600/430; 606/27, 606/28, 31–35, 41; 607/101
See application file for complete search history.

(56) References Cited

U.S. PATENT DOCUMENTS

| | | | |
|---|---|---|---|
| 6,104,959 A * | 8/2000 | Spertell ..................... | 607/101 |
| 7,070,595 B2 | 7/2006 | Ormsby et al. | |
| 7,339,382 B1 * | 3/2008 | Bray et al. ..................... | 324/644 |
| 2006/0155270 A1 * | 7/2006 | Hancock et al. ................ | 606/33 |

(Continued)

FOREIGN PATENT DOCUMENTS

| JP | 62151766 | 7/1987 |
|---|---|---|
| JP | 2001511387 | 8/2001 |

(Continued)

OTHER PUBLICATIONS

International Search Report and Written Opinion for PCT/GB2010/002114 dated Apr. 11, 2011.

(Continued)

*Primary Examiner* — Arleen M Vazquez
*Assistant Examiner* — Neel Shah
(74) *Attorney, Agent, or Firm* — Snell & Wilmer L.L.P.

(57) ABSTRACT

A microwave apparatus comprises a microwave source for providing a microwave signal, connectable to a load; control means configured in operation to vary over a frequency range a frequency of the microwave signal provided by the source; a microwave detector for performing microwave measurements, arranged to receive reflections from and/or transmissions to the load in operation and to perform a plurality of measurements, each measurement corresponding to a respective one of a plurality of different frequencies of the frequency range; and means for determining from the plurality of measurements a measure of reflection and/or a measure of transmission.

24 Claims, 22 Drawing Sheets

(56) References Cited

U.S. PATENT DOCUMENTS

| | | |
|---|---|---|
| 2006/0287649 A1* | 12/2006 | Ormsby et al. ............. 606/33 |
| 2008/0234574 A1* | 9/2008 | Hancock et al. ............ 600/430 |
| 2008/0319434 A1* | 12/2008 | Rick et al. ................. 606/33 |
| 2009/0076492 A1* | 3/2009 | Behnke ....................... 606/33 |
| 2010/0082025 A1* | 4/2010 | Brannan et al. ............ 606/33 |
| 2010/0145328 A1* | 6/2010 | Hancock et al. ............ 606/33 |
| 2010/0228244 A1* | 9/2010 | Hancock et al. ............ 606/33 |
| 2010/0286686 A1* | 11/2010 | Hancock ..................... 606/33 |

FOREIGN PATENT DOCUMENTS

| | | | | |
|---|---|---|---|---|
| WO | 9905978 | | 2/1999 | |
| WO | 2008005668 | | 1/2008 | |
| WO | WO2008/043999 | * | 4/2008 | ............. 324/601 |
| WO | 2008071914 | | 6/2008 | |
| WO | 2009040523 | | 4/2009 | |
| WO | WO2009/040523 | * | 4/2009 | ............. 606/33 |

OTHER PUBLICATIONS

Examination report received in Chinese patent application No. CN101484083 dated Apr. 1, 2014.

Office Action dated Aug. 26, 2014 in Japanese Application No. 2012-539403.

* cited by examiner

100% CW Output power

Example of 50% (average) PWM Output Power

Z0=55 Ohm
L=1500 mm

Z=50 Ohm

Z=100 Ohm

Z0=45 Ohm
L=1500 mm

Z=50 Ohm

Z=100 Ohm

Z0=45 Ohm
L=1530 mm

Z=50 Ohm

Z=100 Ohm

MICROWAVE POWER MONITORING

CROSS-REFERENCE TO RELATED APPLICATIONS

This application is a U.S. national phase filing under 35 U.S.C. §371 of PCT/GB2010/002114 filed Nov. 17, 2010. PCT/GB2010/002114 claims priority from U.S. Provisional Application No. 61/262,206, filed on Nov. 18, 2009. All of the aforementioned applications are incorporated herein by reference.

FIELD OF THE INVENTION

The present invention relates to microwave apparatus and methods, for example apparatus and methods for measuring forward and reflected power at microwave frequencies, including microwave power generator systems and methods that measure forward or reflected power. The apparatus and methods are applicable to both industrial and medical microwave applications.

BACKGROUND TO THE INVENTION

The reflected power measurement of known microwave generator systems is typically used as an indirect mechanism for determining the level of applied power (given that the energy deposited in the target material cannot be easily obtained directly). In the event that a predetermined level of reflected power is exceeded the generator system can quickly and safely be shutdown, preventing damage to the equipment and preventing faulty devices operating due to a system misreading.

In medical applications the measurement of reflected power can act as a safety mechanism to detect and react to device failures, connection issues and some forms of misuse. The advantage of reflection measurements is that blind treatments can be monitored in real time without requiring the user to inspect the treatment site, which could result in additional power being administered, which could inadvertently cause adverse events. Conversely an entirely adequate medical device could accidentally be misinterpreted as being faulty causing the user to abandon a treatment causing unnecessary risk and distress to a patient and requiring the treatment to be rescheduled.

In known apparatus, forward and reverse power circuits are used to measure the energy delivered to and reflected from load components connected to a microwave generator. The accuracy of that measurement is important as it can be used as a safety monitor or to protect amplifier circuitry in the generator from high levels of reflected power that can damage the hardware.

In the case of a load component that reflects a portion of incident microwave energy, a voltage standing wave is established which varies sinusoidally in amplitude with distance (electrical phase length) from the mismatched component. The ratio of the voltage maximum (antinode) to the adjacent voltage minimum (node) on a transmission line is relative to the proportion of the energy reflected and the energy delivered and is called the voltage standing wave ratio (VSWR).

Typically microwave components are designed and measured using vector (magnitude and phase) network measurement equipment where mismatches and measurement-cable phase effects are calibrated out using sophisticated software based calibration techniques. These components are designed and measured against highly accurate 50Ω reference standards. Typically components will differ slightly from the reference standards presenting a mismatch that will cause some minor degree of VSWR. The issue only becomes significant in cases where the component match is poor. In the case of medical applications the applicator to system match is often worse than the typical industrial component return loss of −20 dB (VSWR 1.22:1) which can result in significant levels of VSWR.

For microwave systems that employ a single operating frequency, the reverse power measurement circuitry will only measure a single point of the VSWR sinusoid. As the VSWR sinusoid varies with distance, changes in length of the path will cause the reflected power measurement to follow the profile of the VSWR sinusoid. This effect could cause the reverse power measurement circuit to measure anywhere from a VSWR maximum to a VSWR minimum for two identical mismatched components differing only in phase length. In a system that relies upon measuring the reverse power to denote performance this represents an ambiguous and unreliable measurement.

In known generator systems, microwave power is often measured using detector diodes which provide a voltage related power measurement. These systems are constructed from combinations of components designed and measured against accurate 50Ω impedance reference standards using vector (magnitude and phase) test equipment, however the finished systems are expected to make critical measurements without reference to any form of in situ calibration. Instead, operating characteristics of systems are determined from measured reflected signals (often measured at a single location and frequency) based upon properties of individual components pre-determined against the reference standards. The omission of calibration emphasises the effects of variation and cable phase length upon the power measurement. It is also common practice to generate microwave signals using continuous wave (CW) microwave generators. Such CW generators are often limited to generating microwave energy at a single fixed frequency point, for example 2.45 GHz, due to the use of magnetron based technology that can only provide energy at fixed frequencies. Variation of device physical parameters in conjunction with CW operation and lack of calibration can result in considerable variation in measurements.

Another factor that is overlooked in known systems is the effect of cascaded mismatches. For example, components designed for a 50Ω termination may be connected to other mismatched components and the electrical phase length of the interconnects such as cables or phase length of the applicators may be either ignored or unknown causing mismatch uncertainty. That is an often overlooked source of error in microwave measurements. The design and calibration of equipment, particularly medical equipment should take account of measurement uncertainties to demonstrate competence.

It should be understood that, disregarding the aforementioned effects of VSWR and standing waves on reflected power measurements, the overall power delivered to a load should remain relatively constant irrespective of minor variations in cable length provided the load is of a constant value.

It is known to measure reverse power using a directional coupler connected to a detector diode. VSWR is computed by establishing the ratio of forward to reverse power measured. In most systems reverse power standing wave is measured at a single frequency point. The effect of the standing wave is not evident at this single frequency point measurement until parameters such as match or phase length are varied (as often happens with component manufacturing tolerances).

A limitation in using couplers or impedance dependant measuring components in power detector circuits is that these devices are often suited to measuring against matched terminations. In the case of directional couplers the coupling factor and the directivity will be affected by the impedance presented at the ports of the device. The performance of a detector circuit that uses a coupler or any other arrangement of impedance sensitive components (e.g. coupler/isolator) will be affected by the varying impedance presented to the ports.

This characteristic is acceptable in industrial applications where the device under test (DUT) typically possesses a match of −14 dB or better (VSWR 2:1). In medical applications the applicator or antenna match can differ considerably from 50Ω and may range from −20 dB (VSWR 1.22:1) to −6 dB (VSWR 3.01:1), or worse depending upon the application. The effective impedance of the applicator or antenna can also change as the properties of tissue change during a treatment which requires a measurement system that can accommodate a wide range of impedance variation. This is particularly critical in reflected power measurements where a medical system has been configured to measure reflected power using standard 50Ω reference components. When connected to a new impedance the setup will continue to refer all measurements to the 50Ω reference standard resulting in uncertainty and unreliability of reflected power measurements where the impedance differs from 50Ω. This impedance related measurement limitation may also be subject to the effects of phase which can be reduced using a swept source as described herein or by any other method that takes an average measurement over variations in phase by either mechanically or electrically sweeping the phase. The effect of impedance sensitive measurement variation on its own adds a further independent source of error into power measurements.

Systems that utilise reflected power measurements and determination of VSWRs in monitoring and controlling the application of microwave power for medical applications are described in US20090076492, U.S. Pat. No. 7,070,595, U.S. Ser. No. 11/479,259, and US 20080319434.

US 20090076492 and U.S. Pat. No. 7,070,595 describe adjusting a system parameter, such as phase length, or moving an output frequency, so as to operate at a position of lowest measured VSWR, which is perceived as the optimal operating arrangement. However that approach is flawed in that the overall system performance is not being improved as the antenna impedance remains unchanged and the power delivered remains the same. The only change is that the reference point of the VSWR measurement is moved to a null point at which the reflected signal is partially cancelled against the transmitted signal. Thus, such systems provide for unreliable measurement of reflected power or VSWR, which cannot be relied upon for safety critical purposes.

SUMMARY OF THE INVENTION

In a first, independent aspect of the invention there is provided a microwave apparatus comprising:—a microwave source for providing a microwave signal, connectable to a load; control means configured in operation to vary over a frequency range a frequency of the microwave signal provided by the source; microwave detector for performing microwave measurements, arranged to receive reflections from and/or transmissions to the load in operation and to perform a plurality of measurements, each measurement corresponding to a respective one of a plurality of different frequencies of the frequency range; and means for determining from the plurality of measurements a measure of reflection and/or a measure of transmission. There may be provided a plurality of microwave detectors. The or each microwave detector may comprise a microwave power detector.

By varying the frequency of the microwave signal over a frequency range, a more accurate measure of reflection and/or transmission may be obtained. For example, standing wave effects may be more accurately determined.

The control means may be configured to control at least one property of the microwave signal provided by the microwave source, for example to perform on operation at or by the load. The control means may be configured to vary the frequency of the microwave signal substantially throughout performance of the operation. The operation may comprise an ablation or other heating operation, and for example may be performed on biological tissue.

The varying of the frequency may comprise varying the frequency between a maximum and minimum frequency, the maximum and minimum frequency being the highest and lowest frequencies of the range. The measuring means may be configured to process together and/or compare the plurality of measurements to determine the measure of reflection.

The performance of a measurement corresponding to a frequency of the frequency range of the microwave signal provided by the source may comprise measuring at that frequency. The measurement may comprise for example measuring a received signal arising from reflection of the microwave signal at that frequency provided by the source and/or measuring a received signal substantially simultaneously with the provision of the microwave signal at that frequency by the source.

Each measurement may comprise a measurement of a reflected or transmitted signal alone or may comprise a measurement of a reflected signal superposed with a transmitted signal, for example the signal provided by the source. The microwave detector may be arranged to receive a superposition of reflected and applied radiation. The microwave detector may be controlled, for example by the control means, to perform the plurality of measurements.

The control means may comprise a controller, for example a suitably programmed microprocessor. The controller may be configured to control the at least one property of the microwave signal by applying at least one control signal to the microwave source or to a component, for example an oscillator, filter or amplifier, associated with the microwave source. Alternatively or additionally the control means may comprise a swept frequency oscillator and/or an amplifier.

The load may comprise, for example, an applicator or an aerial.

The microwave source may be connectable to the load via a transmission line such that in operation a voltage standing wave is formed in the transmission line by the superposition of the microwave signal provided by the source and a reflection of the microwave signal, the amplitude of the voltage standing wave (VSW) varying between a maximum and a minimum with position on the transmission line in a VSW cycle, and the frequency range may be such that the varying of the frequency by the control means over the applied frequency range causes the VSW at a location of the microwave detector to vary over at least one VSW cycle.

By varying over at least one VSW cycle, a more complete knowledge of the reflected signal characteristics may be obtained.

The microwave source may be connectable to the load via a transmission line having a length L, and the frequency range may have a width greater than or equal to $c/2L$, wherein $c$ is the speed of light in a vacuum.

It has been found that by varying the frequency over a range of such a width, reflected signals across at least one VSW cycle can be measured.

The frequency range may have a width greater than or equal to 50 MHz, optionally greater than or equal to 200 MHz, optionally greater than or equal to 500 MHz. That width may provide for an accurate measurement of VSW or other standing wave or phase effects.

The frequency range may have a width less than or equal to 1000 MHz, optionally less than or equal to 500 MHz. By limiting the width of the frequency range a faster and more efficient procedure may be provided in some circumstances.

The control means may be configured to vary the frequency of the microwave signal by sweeping the frequency over the frequency range. The sweeping may comprise substantially continuously varying the frequency.

The control means may be configured to vary the frequency of the microwave radiation over the applied frequency range by controlling the signal to have a sequence of different frequencies.

The sequence may be a sequence of predetermined frequencies and/or a sequence of frequencies determined in accordance with a predetermined algorithm, and/or a substantially random sequence of frequencies. The control means may control the signal to hop between the different frequencies in the sequence.

The control means may be configured to repeatedly vary the frequency of the microwave signal over the frequency range. For example, the control means may repeatedly sweep the frequency over the frequency range or may repeat the sequence.

The microwave signal may comprise a pulsed signal or a continuous wave signal.

The microwave signal may comprise a pulsed signal and the control means may be configured to vary the frequency of the signal during each pulse. The control means may be configured to vary the frequency of the signal over the frequency range in a repeating cycle, and the duration of each cycle may be less than the duration of each pulse. The duration of each cycle may be less than or equal to one tenth of the duration of each pulse.

The measure of the reflection obtained for the applied frequency range may be representative of an average or maximum amount of reflection obtained for the frequency range and/or the measure of transmission for the applied frequency range may be representative of an average or maximum amount of transmission obtained for the frequency range. For example, the measure of reflection may be representative of an average or maximum reflected power.

The microwave detector may be further configured to measure the microwave signal provided by the source and a reflection of the microwave signal, and to determine a voltage standing wave ratio (VSWR) from the measured provided signal and the measured reflection.

The microwave detector may be configured to measure the microwave signal provided by the source separately from the reflection, or may be configured to measure the superposition of the microwave signal provided by the source and the reflection.

The measure of the amount of reflection may comprise a VSWR for the frequency range, for example a maximum or average VSWR for the frequency range.

The apparatus may comprise monitoring means configured to compare the measure of the amount of reflection and/or transmission to a threshold.

The control means may be configured to vary at least one property of the microwave signal provided by the source in dependence on the comparison.

The control means may be configured to reduce or increase the power of the microwave signal in dependence on the comparison and/or to halt application of the microwave signal to the load in dependence on the comparison.

The microwave source may comprise an internal microwave signal generator and a swept frequency oscillator. The swept frequency oscillator may have a sweep bandwidth greater than or equal to c/2L.

The microwave source may comprise an external microwave oscillator, an amplifier for amplifying signals from the external microwave oscillator to provide the microwave signal, and means for applying a control signal to the amplifier to control the microwave signal.

The microwave detector may comprise at least one of:—a directional coupler and microwave circulator; a reverse power microwave detector circuit for measuring the reflected power returned towards the generator from the load; a reverse power measurement circuit.

The directional coupler and microwave circulator may have an operational bandwidth of at least c/2L. The reverse power microwave detector circuit may comprise microwave detector diodes. The reverse power measurement circuit may be configured to sample and average the frequency-dependant voltage signal provided by a microwave detector diode to reduce the influence of VSWR on the reflected power signal.

The control means may be configured to provide a pulse width modulated (PWM) output signal to control the average power delivered. The control means may be configured to provide a pulse width modulated (PWM) output signal with an ON/OFF switching frequency less than that of the signal generator sweep frequency.

The microwave source may comprise a swept frequency oscillator and a microwave amplifier, and the control means is configured to drive the microwave amplifier in a linear region of its performance characteristic in operation.

Thus, gain control with substantially continuous output power may be provided.

The microwave signal generator may comprise a swept frequency oscillator having a frequency sweep modulation scheme, for example spread spectrum or frequency hopping.

The microwave source may be connectable to a load comprising a probe or applicator, for example a probe or applicator for applying microwave radiation to biological tissue.

The control means may be configured to control the source in operation to provide a microwave signal to perform an operation, for example an ablation operation, on biological tissue.

The load may be connected to at least one of a microwave coupler and a microwave circulator.

The apparatus may further comprise storage means for storing calibration data that relates measurement values to the value of load impedance, and the control means may be configured to apply a correction to the measurements based upon the calibration data.

The measurement values of the calibration data may comprise at least one of transmitted signal level, reflected signal level and transmission to reflection ratio.

The control means may be configured to control the source in operation to provide the microwave signal having a power in the range 1 W-300 W.

In another independent aspect of the invention there is provided a method of monitoring microwave reflection, comprise providing a microwave signal to a load; varying the frequency of the microwave signal over a frequency range;

performing a plurality of microwave measurements, each at a respective one of a plurality of different frequencies of the frequency range of the microwave signal provided by the source and each comprising a reflection and/or transmission of the microwave signal; and determining from the plurality of measurements a measure of reflection and/or transmission.

The method may further comprise providing the microwave signal to the load via a transmission line, such that in operation a voltage standing wave is formed in the transmission line by the superposition of the microwave signal provided by the source and a reflection of the microwave signal, the amplitude of the voltage standing wave (VSW) varying between a maximum and a minimum with position on the transmission line in a VSW cycle, and the frequency range may be such that the varying of the frequency by the control means over the applied frequency range in operation causes the VSW at a measurement location to vary over at least one VSW cycle.

The microwave signal may be provided to the load via the or a transmission line having a length L, and the frequency range may have a width greater than or equal to c/2L, wherein c is the speed of light.

The method may further comprise varying the frequency of the microwave signal by sweeping the frequency over the frequency range.

The method may further comprise varying the frequency of the microwave signal over the applied frequency range by controlling the signal to have a sequence of different frequencies.

The measure of reflection and/or transmission obtained for the applied frequency range may be representative of an average or maximum amount of reflection and/or transmission obtained for the frequency range.

The method may further comprise measuring the microwave signal provided by the source, measuring a reflection of the microwave signal, and determining a voltage standing wave ratio (VSWR) from the measured provided signal and the measured reflection. The measure of the amount of reflection may comprise a VSWR for the frequency range, for example a maximum or average VSWR for the frequency range.

The method may further comprise comparing the measure of the amount of reflection and/or transmission to a threshold, and varying at least one property of the microwave signal provided by the source in dependence on the comparison.

The method may further comprise replacing the load with a plurality of reference loads, each reference load having a known impedance, and performing calibration measurements for each of the reference loads.

The calibration measurements may comprise measurements of at least one of transmitted signal level, reflected signal level and transmission to reflection ratio.

The method may further comprise applying a correction to the microwave measurements based on the calibration measurements.

The load may be connected to at least one of a microwave coupler and a microwave circulator, and the correction may be such as to compensate the microwave measurements so as to linearize a coupling factor response.

The method may further comprise reducing or increasing the power of the microwave signal in dependence on the comparison and/or halting application of the microwave signal to the load in dependence on the comparison.

In another independent aspect of the invention there is provided a computer program product comprising computer readable instructions executable to perform a method as claimed or described herein.

In a further independent aspect of the invention there is provided a microwave apparatus comprising:—a microwave source for providing a microwave signal, connectable to a load, and configured in operation to vary over a frequency range a frequency of the microwave signal; a microwave detector for performing microwave measurements, arranged to receive reflections from the load in operation and to perform a plurality of measurements, each measurement corresponding to a respective one of a plurality of different frequencies of the frequency range; and a processing device for determining from the plurality of measurements a measure of reflection.

In other independent aspects of the invention there are provided a method and apparatus for measuring reflected microwave power supplied to a microwave generator using a swept operating frequency combined with reflected power averaging to minimise the effects of voltage standing wave ratio on reflected power measurements.

In another independent aspect of the invention there is provided a microwave frequency power generator comprising: an internal microwave signal generator with a swept frequency oscillator having a sweep bandwidth greater than or equal to (C/2×Cable Length); and/or an amplifier having a operational bandwidth of at least (C/2×Cable Length); and/or a directional coupler and microwave circulator having a operational bandwidth of at least (C/2×Cable Length); and a reverse power microwave detector circuit utilizing microwave detector diodes to measure the reflected power returned towards the generator from the load; and/or a reverse power measurement circuit to sample and average the frequency-dependant voltage signal provided by a microwave detector diode to reduce the influence of VSWR on the reflected power signal.

The device may have a pulse width modulated (PWM) output signal to control the average power delivered. The device may have a pulse width modulated (PWM) output signal with an ON/OFF switching frequency less than that of the signal generator sweep frequency.

The device may be supplied by an internal swept frequency oscillator such that the microwave amplifier is driven in the linear region of its performance characteristic allowing for gain control with continuous output power.

The device may have a microwave signal generator possessing a swept frequency oscillator having a frequency sweep modulation scheme such as spread spectrum or frequency hopping.

In another independent aspect of the invention there is provided a microwave frequency power generator comprising: an internal microwave signal generator with a variable frequency oscillator having a sweep bandwidth greater than or equal to (C/2×Cable Length); and/or an external microwave signal generator with a variable frequency oscillator having a sweep bandwidth greater than or equal to (C/2× Cable Length); and an amplifier having a operational bandwidth of at least (C/2×Cable Length); and a directional coupler having a operational bandwidth of at least (C/2×Cable Length); and a reverse power microwave detector circuit utilizing microwave detector diodes to measure the reflected power returned towards the generator from the load; and a reverse power measurement circuit to sample and average the frequency-dependant voltage signal provided by a microwave detector diode for the purpose of reducing the influence of VSWR on the reflected power signal.

The device may have a pulse width modulated (PWM) output signal to control the average power delivered. The device may have a pulse width modulated (PWM) output signal with an ON/OFF switching frequency less than that of the signal generator sweep frequency.

The device may be switchable between an internal or an external microwave signal generator. The device may be supplied by a swept frequency oscillator such that the microwave amplifier is driven in the linear region of its performance characteristic allowing for gain control with continuous output power. The device may be supplied by a swept frequency oscillator having a frequency sweep modulation scheme, for example spread spectrum or frequency hopping.

There may also be provided a method and apparatus for measuring reflected microwave power supplied to a microwave generator where the impedance of the load affects the measurement of the ratio of forward power to reflected power.

The ratio can be measured for a plurality of port impedance reference standards, for example impedances such as −1.5 dB, −3 dB, −6 dB −12 db, −20 dB, an electrical open circuit, an electrical short circuit where the ratio is measured for the same power at the input to the directional coupler. This ratio vs. impedance performance can be non linear and can be corrected using a control means, which may comprise a linearization circuit or microprocessor based lookup table to provide a coupling factor that is not output impedance dependent.

The measured ratio signal can be used to determine the port impedance of a connected device and with this knowledge used to generate a signal that can be used as a control means such as a linearization circuit or microprocessor based lookup table to correct a measured signal that would otherwise be influenced by the port impedance thus providing a more accurate measurement.

In another independent aspect of the invention there is provided a method of monitoring microwave transmission or reflection, comprising:—providing a microwave signal to a load connected to a microwave coupler and/or microwave circulator; performing a plurality of microwave measurements, each at a respective one of a plurality of different impedance range and each comprising the transmission and reflection of the microwave signal; and determining from the plurality of measurements a measure of the transmission to reflection ratio relating to the load impedance. The method may comprise using the transmission to reflection ratio versus load impedance relationship to compensate measurements taken using a microwave coupler to linearize the coupling factor response.

There may also be provided an apparatus or method substantially as described herein with reference to the accompanying drawings.

Any feature in one aspect of the invention may be applied to other aspects of the invention, in any appropriate combination. For example, apparatus features may be applied to method features and vice versa.

DETAILED DESCRIPTION OF EMBODIMENTS

Embodiments of the invention are now described, by way of non-limiting example, and are illustrated in the following figures, in which.

Figure 1:
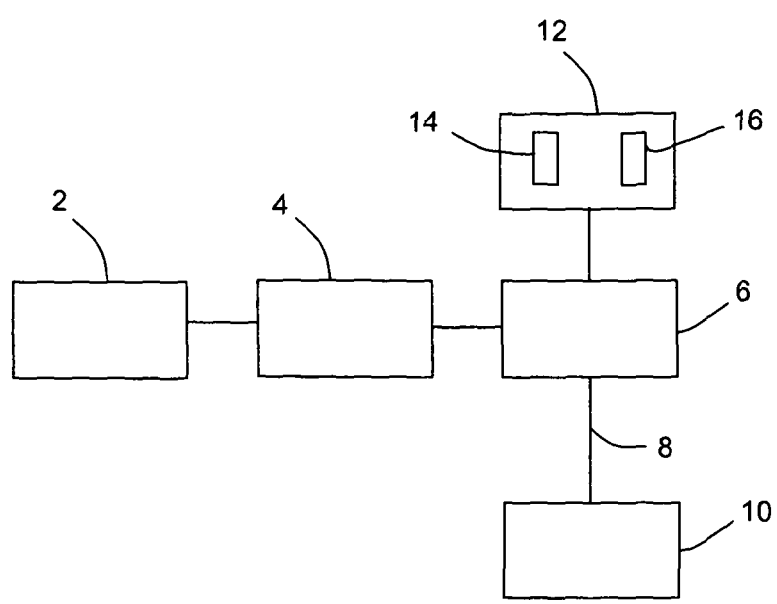
FIG. 1 is a schematic illustration of an embodiment of a microwave system.

An embodiment of a microwave power generator system for medical applications is illustrated in FIG. 1.

The system comprises a microwave source comprising an oscillator 2 (in this case, a Micronetics M3500-2032) operable to generate a high frequency alternating signal, usually at a low power level (up to +10 dBm), and an amplifier 4 (in this case, an Empower BBM3T6AMQ) connected to the oscillator 2 and operable to amplify the low power oscillator signal to a higher power level (for example 20-200 W) and having either SMA or N-Type coaxial inputs or outputs. Any suitable oscillator can be used, for example any dielectric resonator oscillator (DRO) or any crystal oscillator (XO) provided they possess the desired frequency bandwidth.

The amplifier 4 is connected to a microwave circulator 6 (in this case, an MECA CS-2.500), which permit the flow of signals in one direction and a microwave coupler (in this case, an MECA 722N-30-3.100) which provides a sample of the signal on an isolated port (not shown).

The microwave coupler and microwave circulator 6 is connectable to a transmission line 8, in the form of high frequency coaxial cable (for example having 50Ω impedance, in this case Huber+Suhner SUCOFLEX 400) in the illustrated embodiment, having a physical length (and associated electrical phase length), which is arranged to deliver high power energy to a load 10. The load 10 may, for example, be an absorber such as a resistive load (in this case MECA N-Male Termination: CTN-250-1) or radiator of energy such as an antenna, probe or applicator (in this case an Azwell TE-18B microwave applicator) for use in applying radiation to an absorbing medium such as tissue or any other material.

In the embodiment of FIG. 1 the load 10 comprises a probe for applying microwave radiation to biological tissue to perform an ablation procedure on the biological tissue. Other possible applications include applying energy to any other material for heating or drying purposes such as drying of grain or wood pulp or any other processed material with high moisture content. Similarly microwave energy can be applied to materials as part of chemical processing techniques or in ceramic sintering processes.

The system also comprises a controller 12, which is operable to control operation of the oscillator and/or the amplifier, thereby to control one or more properties of the microwave radiation generated by the microwave source. The controller 12 includes forward and reverse power measurement circuits 14, 16 that comprise diode detector devices (in this case, an Agilent 33330C Option 003) that are operable to measure forward and reverse signals at the port of the microwave coupler 6. In operation the forward and reverse power measurement circuits provide power dependent output voltages which are either measured in real-time within a standard comparator circuit or sampled and digitised (e.g. sample rate could be from 20 -200 KHz) and analysed by the controller 12.

Although details of each of the oscillator, amplifier, coupler, circulator, cable and load used in the embodiment are FIG. 1 are provided above, included manufacturer and model numbers, any suitable components can be used, and embodiments are not limited to the particular components described in relation to FIG. 1.

In operation a microwave signal of desired power and frequency characteristics is applied to the load 10 via the transmission line 8, under control of the controller 12. The power and frequency characteristics are usually selected by the controller in order to provide for performance of a desired operation at or by the load. In the embodiment of FIG. 1, the power and frequency characteristics are selected to provide a desired heating effect at a region of biological tissue in order to perform an ablation operation on the region of the tissue.

During application of the microwave signal to the load, the component of the applied signal that is reflected back from the load is measured by the reverse power measurement circuit 14 and monitored by the controller 12. The signal applied via the transmission line is measured, by the forward power measurement circuit 16. The controller 12 can use the measured reflected and applied signals to determine a value for the VSWR, which gives an indication of the impedance matching of the generator to the load. In alternative embodiments, measurement circuitry measures a superposition of the reflected and applied signals rather than measuring the reflected and applied signals separately.

Variation in the determined VSWR, for example above or below a predetermined threshold, can provide an indication of a fault or can provide an indication of the progress of an operation performed at or by the load (for example the level of ablation of a region of tissue). In some cases, variation in the VSWR can indicate that tissue or other material under treatment, or a component of the apparatus is overheating and in that case the controller 12 is configured to halt the application of the microwave signal, or to reduce the microwave signal power. Thus, the correct measurement of the reflected signal level and/or VSWR is important for safe operation of the apparatus.

It is a feature of the embodiment of FIG. 1 that the controller 12 is configured to control operation of the microwave source so that the frequency of the applied microwave signal is varied during application, and during the monitoring of the applied and reflected signals, so that the applied and reflected signals are measured at a plurality of applied frequencies.

As discussed in more detail below, it is a feature of practical microwave systems that the measured voltage at any point on the transmission line is a superposition of the applied and reflected signals (also referred to as the forward and reflected waves) and that the amplitude of the superposed applied and reflected signals varies with position on the transmission path, following a VSWR sinusoid or other wave form. The reverse power measurement circuitry will only measure a single point of the VSWR waveform, and as the VSWR sinusoid varies with distance, changes in length of the path will cause the reflected power measurement to follow the profile of the VSWR sinusoid. This effect could cause the reverse power measurement circuit to measure anywhere from a VSWR maximum to a VSWR minimum for two identical mismatched components.

However, by varying the frequency of the applied signal whilst monitoring the applied and reflected signals the electrical phase can be varied at the measurement location, which can have the same effect as varying the length of the transmission line.

In the embodiment of FIG. 1, the controller 12 is configured to vary the applied frequency so that the measurement circuitry samples the applied and reflected signals across a full VSWR cycle.

The controller 12 is able to control operation of the microwave source in dependence on a measure of the amount of reflected radiation determined from the sampled reflected and/or applied signals.

In one mode of operation, the controller 12 averages the reflected signals obtained for each frequency sweep, or across multiple frequency sweeps to obtain the measure of reflected radiation. In another mode of operation, the controller determines the ratio of reflected to transmitted signal amplitudes at each sampled frequency, and averages the determined ratio of reflected to transmitted signal amplitude for each frequency sweep or across multiple frequency sweeps, to obtain the measure of reflected radiation. In another mode of operation, the controller 12 calculates a value for the VSWR using sampled measurements across the range of frequencies and uses the calculated value of the VSWR as the measure of the amount of reflected radiation.

Figure 2A:
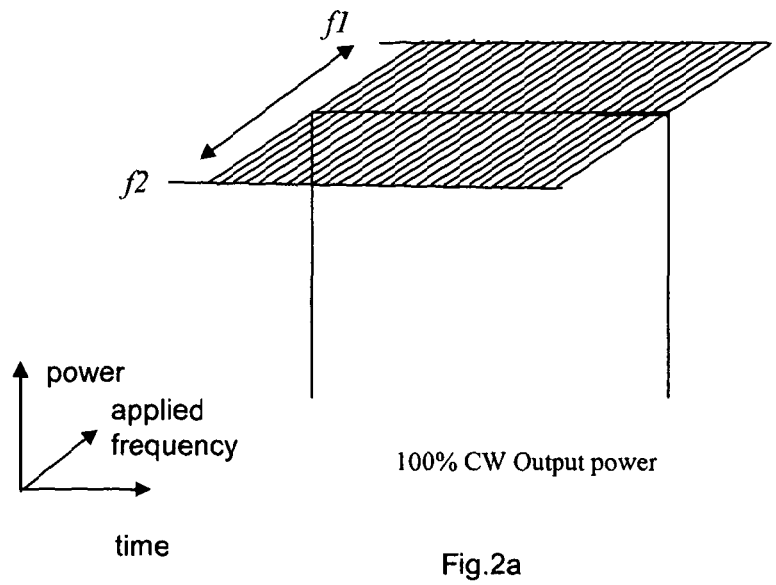
FIGS. 2a and 2b are schematic illustrations of a variation of output power and applied frequency with time, for continuous wave and pulsed outputs.

In the embodiment described above in relation to FIG. 1, the applied microwave radiation is continuous wave radiation (subject to interruption by the controller 12 if the reflected power levels exceed predetermined thresholds). The variation of output power and applied frequency with time is illustrated schematically in FIG. 2a.

Figure 2B:
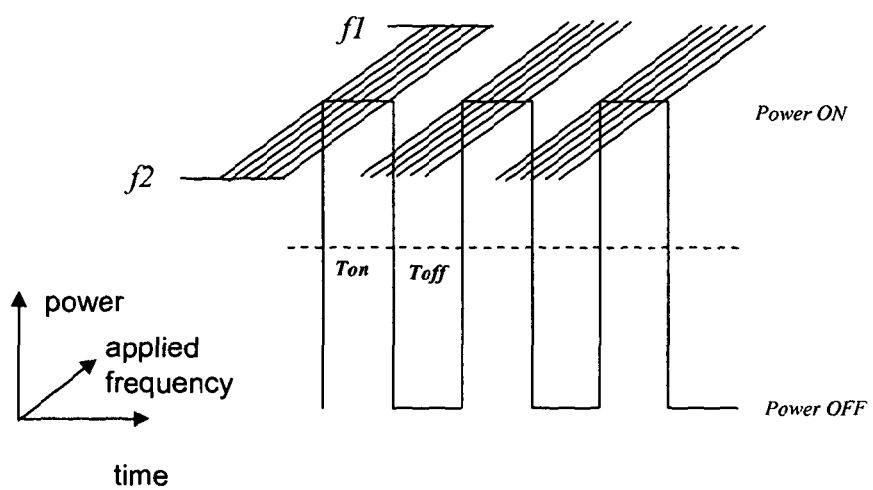

In an alternative embodiment, the apparatus comprise a swept frequency microwave source that has pulse width modulation control of the saturated output power to provide variable output power control. The variation of output power and applied frequency with time for that alternative embodiment is illustrated schematically in FIG. 2b. In this embodiment the controller 12 is configured to continuously sweep the applied frequency between two frequencies f1 and f2 whilst the power output is switched temporally (during successive periods Ton & Toff) so that the applied signal is pulsed at a pulse repetition frequency (the Ton/Toff frequency) and provides a pseudo average power level. The sweep frequency is the frequency with which the applied frequency is varied between f1 and f2.

The f1 to f2 sweep frequency fs is usually greater than the pulse width modulation (PWM) Ton/Toff frequency. For example, in one mode of operation a 1 kHz PWM On/Off signal has a f1 to f2 sweep frequency of 10 kHz to accommodate higher Off/On ratios required for low output power. Any suitable sweep frequencies and pulse repetition frequencies may be used. Usually the sweep frequency is significantly greater than the pulse repetition frequency, in some cases 10 times or more the pulse repetition frequency.

Figure 3:
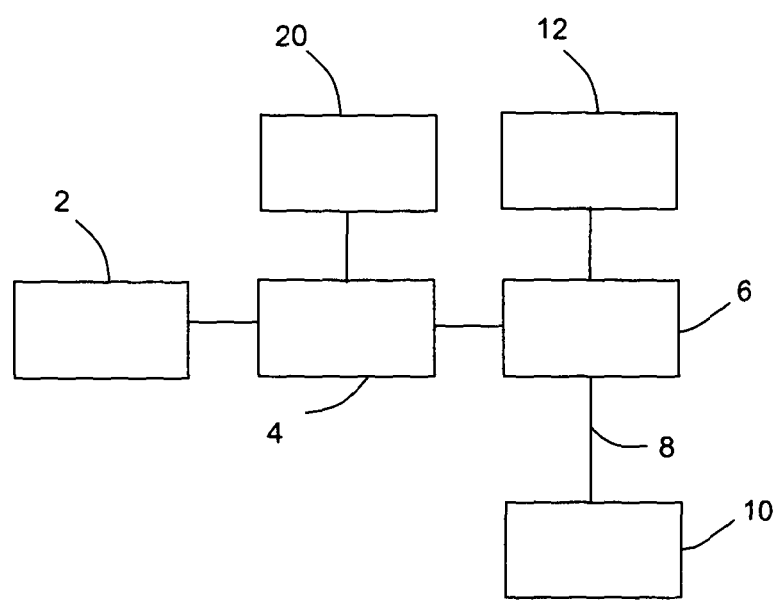
FIG. 3 is a schematic illustration of a microwave system according to an alternative embodiment.

A further alternative embodiment is illustrated in FIG. 3, and comprises an external signal generator 20 that is connected to the amplifier 4 to provide a microwave frequency input signal. The amplifier 4 amplifies the combination of signals from the external signal generator 20 and the swept frequency signal generator 2. In a further alternative embodiment, the swept frequency signal generator 2 is omitted, and the external signal generator is an external swept frequency signal generator for example a Gigatronics 2500A, a Hittite HMC-T1000 or a NovaSource G6.

In a further alternative embodiment, the wide band amplifier 4 is driven in the linear region to provide gain control providing a variable power continuous output signal as opposed to the saturated PWM output. That allows the wide band amplifier to apply various types of signal modulation schemes other than frequency sweeps to the applied microwave signal (for example, spread spectrum, or frequency hopping) for example, optionally under control of the controller 12.

Different combinations of oscillator and amplifier operating conditions can be particularly well suited to provide microwave signals with particular characteristics. For example, an internal oscillator and a saturated amplifier can be used to provide PWM output power, an internal oscillator and a linear amplifier can be used to provide continuous variable output power including modulation schemes, an external oscillator and a saturated amplifier can be used to provide PWM variable output power, and an external oscillator and a linear amplifier can be used to provide continuous variable output power including modulation schemes.

Figure 4:
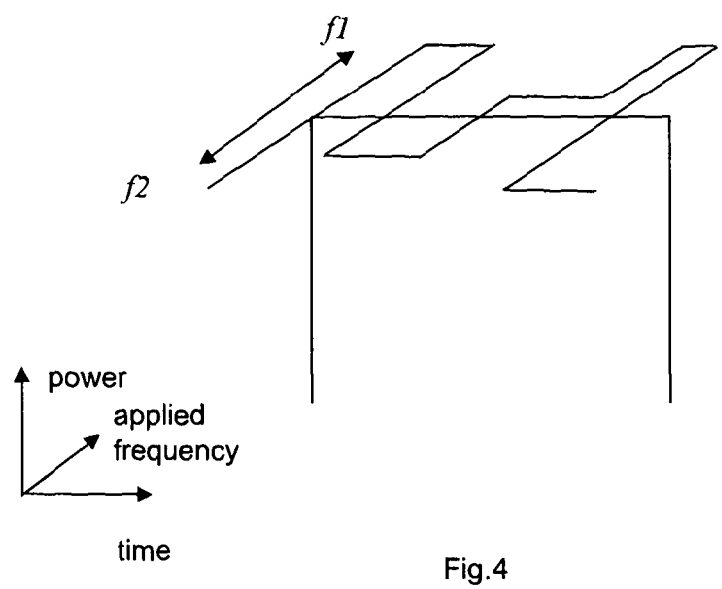
FIG. 4 is a schematic illustration of the variation of output power and applied frequency with time, for a frequency hopping modulation scheme.

An example of variation of output power and applied frequency with time for a portion of such a signal modulation scheme is illustrated schematically in FIG. 4 (in the full modulation scheme a greater number of different applied frequencies would be provided than shown in FIG. 4). In each of the signal modulation schemes, the frequency of the applied microwave signal varies over time within a predetermined frequency range. As was the case with the frequency sweeping, the use of such signal modulation schemes can enable sampling of reflected signals for a plurality of applied signal frequencies, which may enable a more accurate determination of reflected power than measurements at a single applied signal frequency.

Examples of some experimental measurements performed using frequency sweeps, and the effect of such frequency sweeps on the measurement of reflected power are described in more detail below. Before describing the experimental measurements, some theoretical background is provided.

The case of a system impedance $Z_0$ connected to a load impedance $Z_L$ is considered first. Unless the load impedance is perfectly matched to the system impedance, a proportion of any applied signal will be reflected by the load impedance (the proportion being represented by a reflection coefficient, $\Gamma$) and a standing wave made up of the superposition of applied and reflected signals will be generated having a characteristic voltage standing wave ratio (VSWR). The value of the VSWR is provided by equation (1):

$$VSWR = \left|\frac{1-|\Gamma|}{1+|\Gamma|}\right| \quad (1)$$

where $$|\Gamma| = \left|\frac{Z_L - Z_0}{Z_L + Z_0}\right| \quad (2)$$

The return loss is provided by the following equation:

$$\text{Return loss} = -20 * \log\left(\frac{VSWR-1}{VSWR+1}\right) \quad (3)$$

Considering now the case where the load impedance comprises a termination impedance (B) connected to the source via a characteristic impedance (A), then depending on whether the termination impedance is greater than or less than the characteristic impedance (in most cases 50Ω or 75Ω) a VSWR ripple will occur across the frequency band. A VSWR ($V_1$) will occur due to the mismatch between both the source and the characteristic impedance (with reflection coefficient $\Gamma_A$) and a further VSWR ($V_2$) will occur due to a mismatch between the characteristic impedance and the termination impedance (with reflection coefficient $\Gamma_B$).

The maximum and minimum "peak values" of the VSWR ripple are related as follows:

$$\in A = 20*\log(1 \pm |\Gamma_A * \Gamma_B|) dB \quad (4)$$

where $\in A$=VSWR amplitude error

The resultant MIN and MAX for cascaded VSWR amplitudes are given by the following:

$$VSWR\ MAX = V_L * V_S \quad (5)$$

$$VSWR\ MIN = V_L / V_S \quad (6)$$

where:
  $V_L$=larger of the two VSWRs (either $V_1$ or $V_2$)
  $V_S$=smaller of the two VSWRs (either $V_1$ or $V_2$)

A series of graphs are provided in FIGS. 5 to 12, in which the simulated frequency vs. return loss response for ideal circuit components is plotted for a standard cable having a better than −20 dB return loss (VSWR 1.22:1) connected to a termination of −9.54 dB (VSWR 2:1) for various lengths of cable, cable impedances, and values of termination impedance, all with respect to a 50Ω input impedance. Using the above theory (with mismatch uncertainty and mismatch loss omitted):
  $V_L$=2:1, $V_S$=1.22
  VSWR MAX=2.44:1=−7.5 dB (wrt 50Ω)
  VSWR MIN=1.63:1=−12.4 dB (wrt 50Ω)

For each of FIGS. 5 to 12, the graphs provided plot return loss as a function of applied frequency. In each case, a marker on the graph indicates the value of return loss that would be obtained if measurements were performed at a single frequency (in each case 2.45 GHz) and is indicative of the result that would be obtained by measuring a CW signal at that frequency. In each figure the values of the input impedance, cable length, cable impedance and termination impedance are indicated in a schematic circuit diagram next to the graph.

Figure 5A:
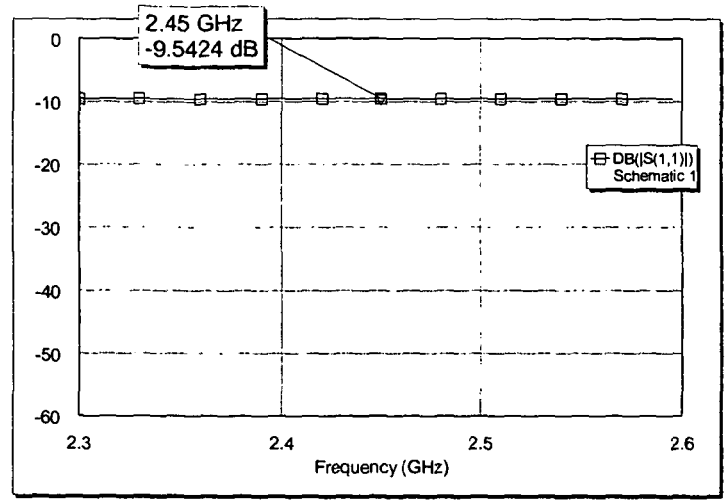
FIGS. 5 to 12 are graphs of return loss as a function of applied frequency for various combinations of input impedance, transmission line impedance and termination impedance.
Figure 5B:
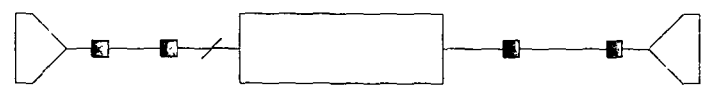

The circuit in FIG. 5 represents a 100Ω load connected directly to a 50Ω source. The simulated transmission line has zero length and does not introduce phase or impedance between the load and source. In this ideal case the return loss is constant across the frequency band. This is similar to a perfectly calibrated measurement, i.e. removal of the effects of the transmission line.

Figure 6A:
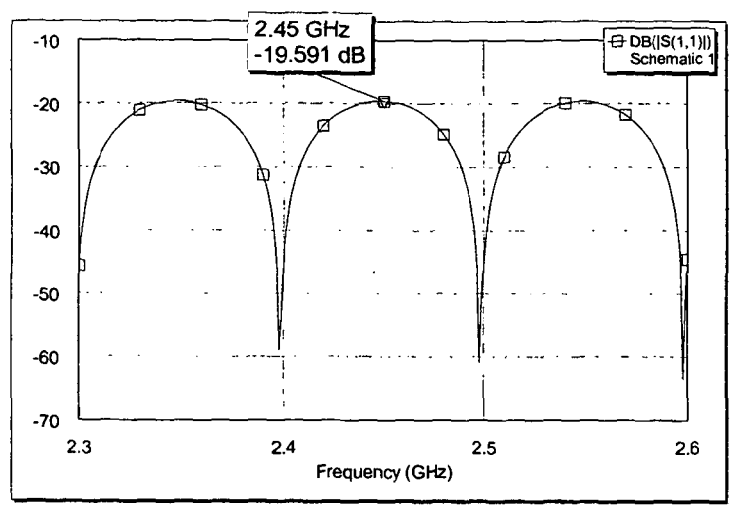
Figure 6B:
Figure 7A:
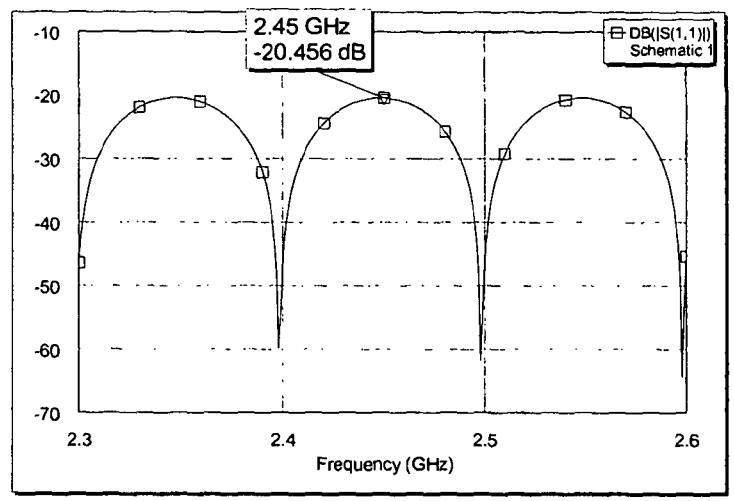
Figure 7B:
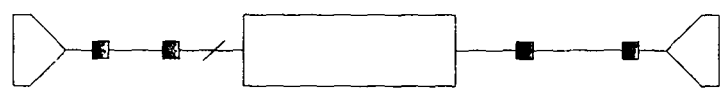

Further circuits and corresponding return loss characteristics are represented in FIGS. 6 and 7, for which the transmission line length is equal to 1.5 m. For each circuit the termination impedance (50Ω) matches the input impedance (50Ω) but there is a mismatch with the transmission line impedance.

Figure 8A:
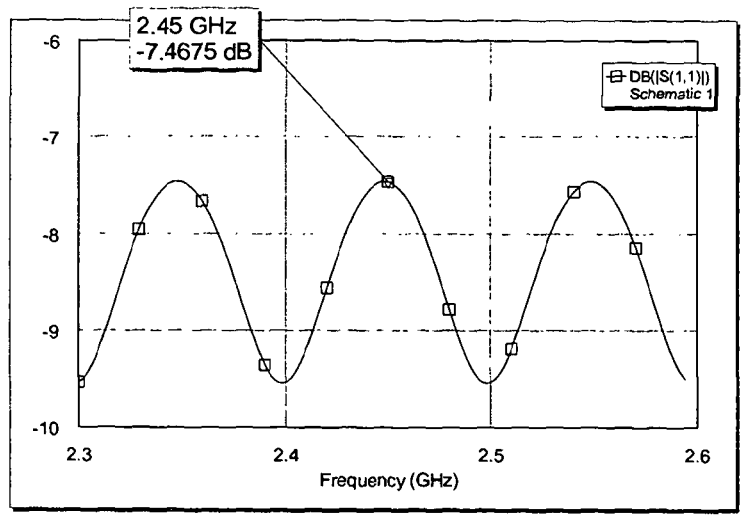
Figure 8B:
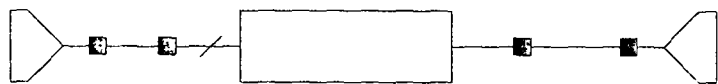

In the circuit of FIG. 8 there are cascading mismatches, between the input impedance (50Ω), the transmission line (45Ω) and the termination impedance (100Ω). The resulting microwave return loss ripple vs. frequency can be seen in FIG. 8, which shows the return loss and VSWR ripple across the frequency band.

Where the line impedance mismatch is greater than the characteristic impedance the VSWR ripple will be below the intrinsic mismatch value and vice versa if the line impedance is less e.g. 45Ω/50Ω or 55Ω/50Ω. That is evident in FIG. 8 where the line impedance is less than 50Ω, the intrinsic mismatch value is −9.5 dB (VSWR=2:1) and the ripple rises to −7.46 dB.

Figure 9A:
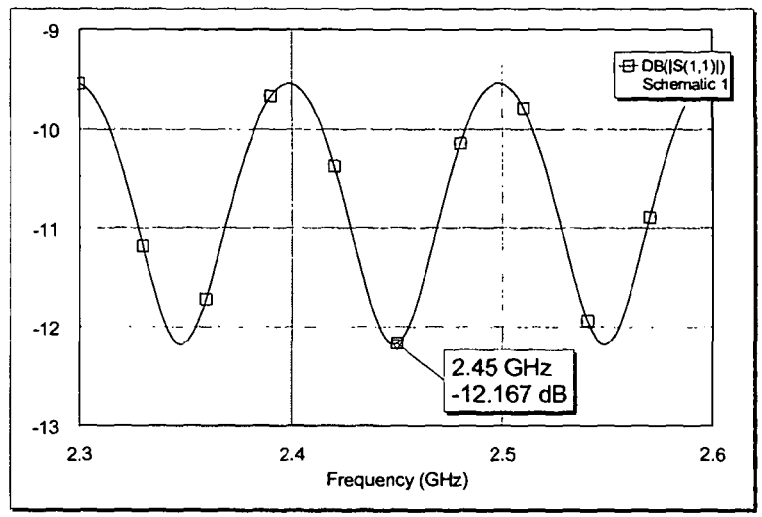
Figure 9B:

The case where the line impedance is greater than 50Ω is illustrated in FIG. 9, in this case the ripple drops to −12.167 dB, again the VSWR is 2:1, and the ripple swings below the intrinsic mismatch value of −9.5 dB.

The two examples of FIGS. 8 and 9, highlight the issue of measurement uncertainty in return loss measurements. In both cases, the input impedance (50Ω) and the termination impedance (100Ω) are the same and would be expected to produce the same VSWR. However, the variation in impedance of the transmission line has a significant effect. It can be seen that a return loss measurement performed at a single frequency of 2.45 GHz (such as in CW operation) would produce very different results in the two cases.

In previously known medical and other microwave systems return loss measurements are usually made using a circulator, coupler and a detector diode and it is often perceived that measuring a low return loss value, (i.e. values near a node) represents optimal performance. However it should be understood that the node is the result of forward and a reflected signals cancelling at the point of measurement and is not indicative of an optimal match elsewhere.

Figure 10A:
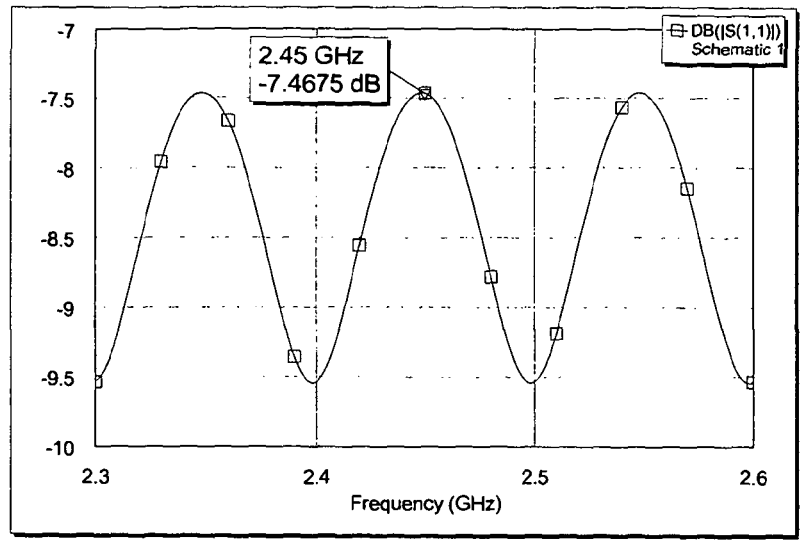
Figure 10B:
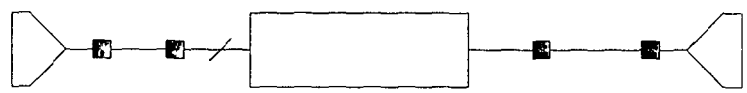
Figure 11A:
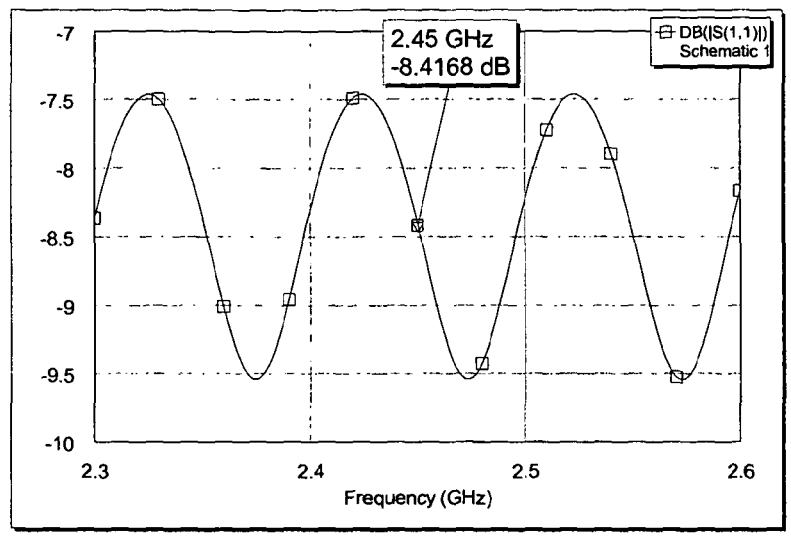
Figure 11B:
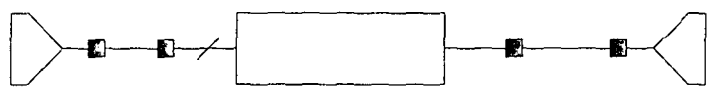
Figure 12A:
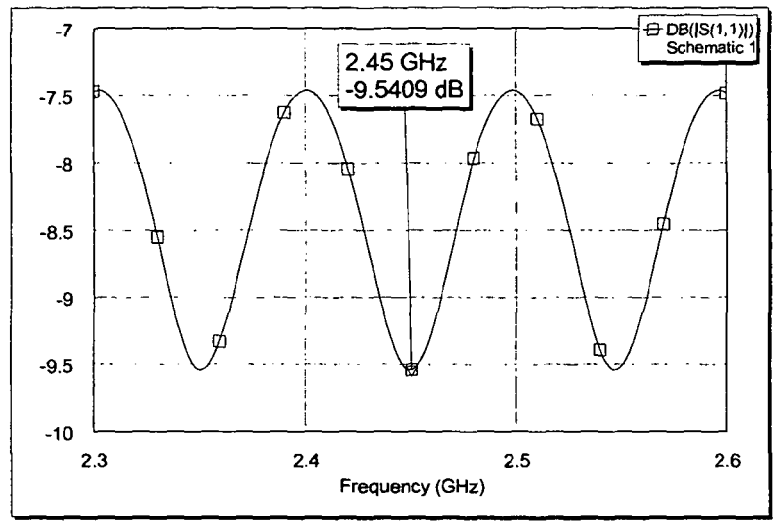
Figure 12B:

It has been found that variations in the length of the cable or other transmission line cause the VSWR ripple to move in frequency, thus changing the value observed at the single measurement point. This is illustrated by modifying the length of the transmission line by +/−1% as illustrated in FIGS. 10 to 12. In each of FIGS. 10 to 12, the values of the input impedance, the transmission line impedance and the termination impedance are the same, but the length of the transmission line is varied between 1.5 m, 1.515 m and 1.53 m. It can be seen that the measured signal at any particular frequency (for example, a fixed frequency of 2.45 GHz) at a single measurement point varies between a maximum and a minimum for that change of +/−1%. This demonstrates that small changes in the physical properties of the cable can significantly change the return loss measurement.

The VSWR ripple is also related to the path length (electrical phase) and signal propagation speed. This relationship is employed by known distance to fault (DTF) performance verification and failure analysis tools which uses a Frequency Domain Reflectometry (FDR) measurement technique to calculate the distance of an impedance mismatch on a line by measuring the frequency difference between corresponding points in the VSWR ripple. This relationship can be summarised as:

$$\text{Length} = V_f \times (c/(2 \times F_s)) \quad (7)$$

where:
Length=physical length of the transmission line.
$V_f$=speed of propagation through the line as a % of speed on light.
c=speed of light in a vacuum (meters per second).
$F_s$=frequency sweep.

Over very short distances the propagation velocity has limited influence on the measurement and as the length is known the above equation can be approximated and rearranged to give:

$$F_s = (c/2 \times \text{Length}) \quad (8)$$

In order to examine the relationship between frequency sweep and cable length, the VSWR performance of various cable lengths were simulated across a number of frequencies. The frequency sweep required to capture at least one full VSWR MAX−MIN cycle was recorded along with the entire sample average. The results are provided in FIG. 13, in which the minimum frequency sweep bandwidth required to capture a full VSWR cycle is plotted as a function of cable length, for cable lengths between 1 m and 3 m. Results are plotted separately for applied frequencies of 2.45 GHz, 5.8 GHz, and 10 GHz.

Figure 13:
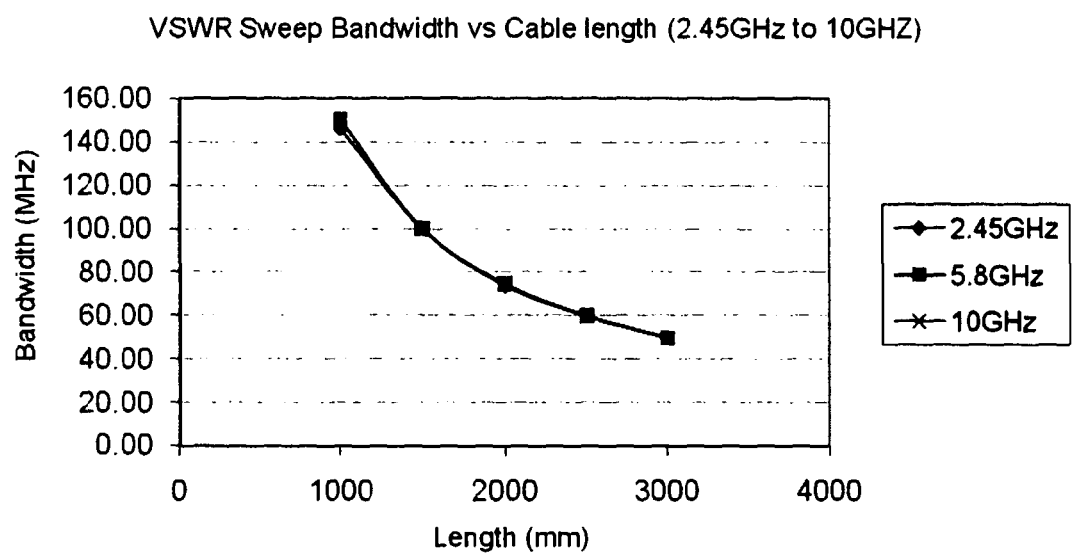
FIG. 13 is a graph of the minimum frequency sweep bandwidth required to capture a full VSWR cycle, as a function of cable length.

It has been found that, as illustrated in FIG. 13, usually a minimum sample bandwidth of c (the speed of light) divided by twice the cable or other transmission line length is required to provide enough data to cover a full VSWR min-max cycle. For example in one embodiment a 1m cable would require a minimum frequency sweep of 150 MHz.

In most practical systems, the frequency of operation is fixed (CW) however the applicator (or other load) impedance match (which changes as the treatment continues) and the cable length are variables and can be dependent on dimensional tolerances of component batches. The difference between the maxima and minima levels is an indication of the measurement uncertainty. As the applicator match decreases, these peaks increase more with a resultant offset (related to the actual return loss).

As an example, for the cable applicator configuration illustrated in FIG. 1, if operated at a fixed frequency, without sweeping or otherwise varying the frequency, a 2% tolerance on cable length results in a variation of the measured return loss from −7.47 dB to −9.54 dB at 2.45 GHz due to the VSWR effect. As a percentage, this is a possible measurement error of 15%, which is significant, coupled with the uncertainty provided by a cable with line impedance greater than 50Ω a return loss as low as −12.167 dB could be measured. This means that 2% error in length of coaxial cables possessing acceptable performance could provide a total measurement uncertainty of approximately 30% for the same applicator. By sweeping or otherwise varying the frequency as describe above in relation to FIG. 1, such errors can be significantly reduced or substantially eliminated.

Figure 14:
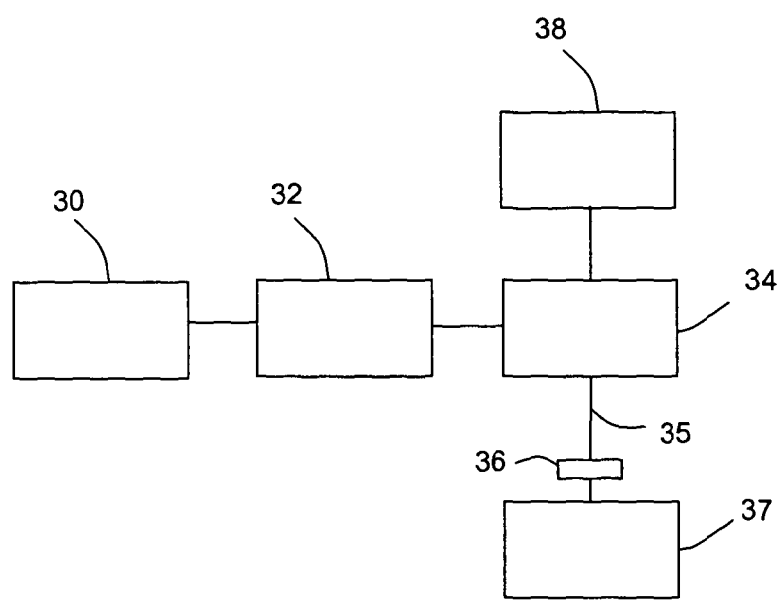
FIG. 14 is a schematic illustration of an embodiment used to perform experimental measurements to illustrate effects of variation in transmission line length.

Further measurements were performed using the arrangement illustrated in FIG. 14. The arrangement is similar to that of the embodiment of FIG. 1. A swept frequency microwave source 30 was connected to a wide band microwave amplifier 32 which was connected through a wideband 30 dB directional coupler 34 to a variable length transmission line 35, which comprised a standard 1.5 m length of 50Ω coaxial microwave cable 11 and a microwave phase shifter 36 (0-360 degrees electrical phase) connected to a load termination 37 having a −12 dB return loss and VSWR of 1.67:1, similar to that of a medical applicator. A controller 38 was provided and included a power detector comprising forward and reverse power measurement circuits (not shown) that comprised diode detector devices operable to measure forward and reverse signals from the coupler 34.

The phase shifter 36 was used to simulate the effect of various electrical lengths of cables. The phase shifter 36 was incrementally cycled through 360 degrees (to simulate the effect of varying the length of the cable) for various output frequencies whilst the voltage on the power detector was recorded using a standard digital voltmeter (Fluke 179). Initially a continuous wave (CW) signal at 2.45 GHz was used to demonstrate the performance that might be expected in the absence of frequency sweep or other variation. This was followed by the application of a variable frequency signal centred around 2.45 GHz with a sweep spanning 2.425 GHz-2.475 GHz increased incrementally to 2.35 GHz-2.55GHz (thus, with a frequency sweep width varying from 50 MHz to 200 MHz).

Figure 15:
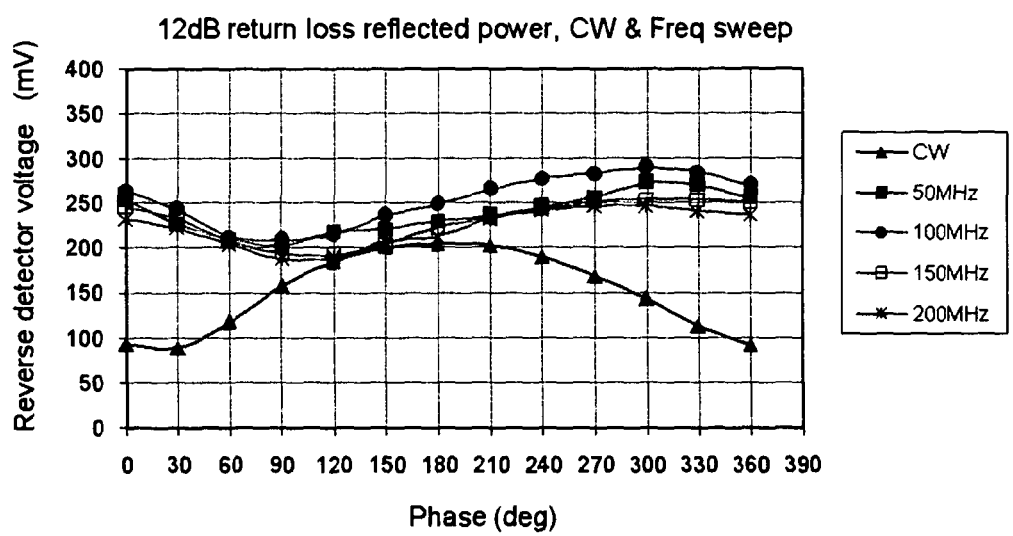
FIG. 15 is a graph of measured reflected microwave signal as a function of phase variation applied by the phase shifter (corresponding to a variation in cable length) for various frequency sweep widths.

The measured reflected microwave signal is plotted as a function of phase variation applied by the phase shifter (corresponding to a variation in cable length) for various frequency sweep widths in FIG. 15. It can be seen that the size of the sweep ripple is reduced significantly for swept frequency measurements compared to CW measurements.

Figure 16:
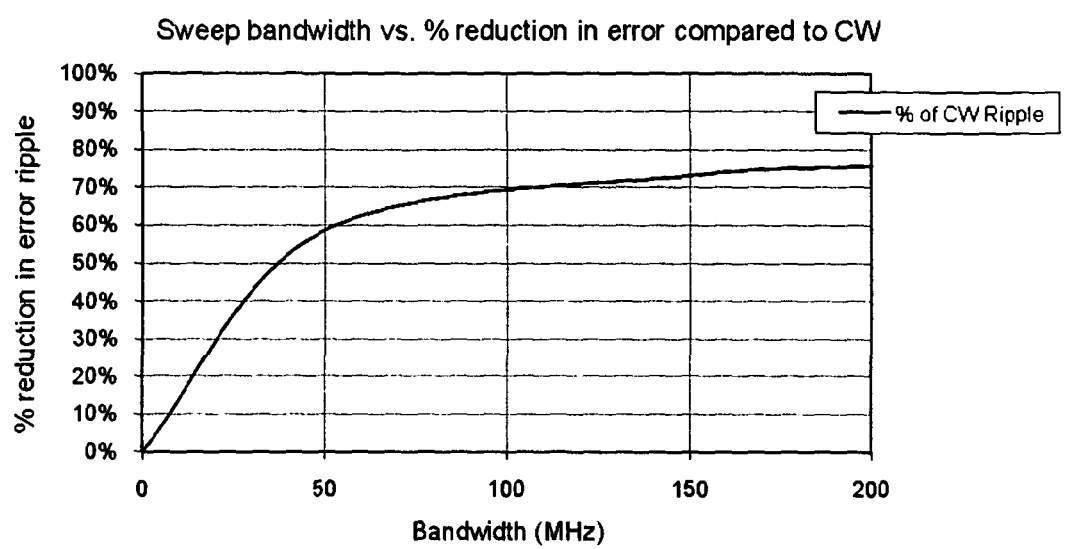
FIG. 16 is a graph of measured percentage reduction in sweep ripple compared with a CW ripple, as a function of sweep width.

The measured percentage reduction in the sweep ripple compared with the CW ripple is displayed FIG. 16. Again it is evident that increasing the sweep bandwidth can produce a significant percentage reduction in ripple.

It can be seen from FIGS. 15 and 16, for example, that a significant improvement in measurement accuracy can be obtained by sweeping or otherwise varying the frequency of applied radiation whilst monitoring reflected radiation. The measured ripple deviation against phase is reduced as the sweep bandwidth is increased. This represents a truer measurement of the delivered power than obtained for CW measurements and is akin to averaging or partial calibration of the effect of cable phase.

Figure 17A:
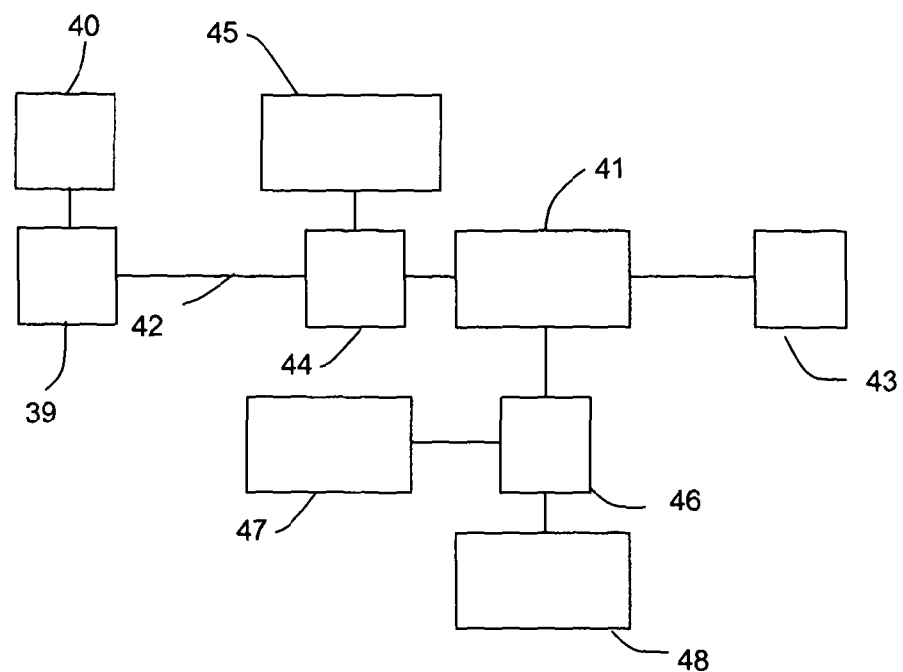
FIG. 17a is a schematic illustration of an embodiment used to perform forward and reverse power measurements.

A further embodiment of microwave power system is illustrated in FIG. 17*a*, which shows components of forward and reflected power measurement circuits in more detail.

The system includes a microwave source 39 and associated controller 40 connected to an input port 42. The source 39 is operable to apply microwave signals to the input port and to sweep or otherwise vary the frequency of the microwave signals as already described. The controller 40, that comprises for example analogue control circuitry or digital control circuitry or a dedicated microprocessor or suitably programmed and interfaced computer, is operable to control operation of the microwave source, for example to control the power and frequency levels of the microwave signals provided by the source 39. The controller 40 is also connected to other components of the system, including the detectors 45, 47 described below and is operable to process, store and apply corrections to measurements by those other components if desired.

The input port 42 is connected to a coupler 44 that is connected in turn to a detector 45 and to a circulator 41. The circulator 41 is connected to a load 43, for example a microwave applicator and to reflected power measurement components. The reflected power measurement components comprise a coupler 46 that is connected both to a detector 47 and to a reflected power termination 48. Any suitable devices can be used as the different components, for example the same or similar devices (for instance the same manufacturer and model numbers) as described in relation to the embodiments of FIGS. 1 and 3 can be used for the various components.

In the embodiment of FIG. 17*a*, as well as varying the frequency of the microwave signal during operation, a calibration is also used according to which the performance of the system when connected to a variety of different standard impedances is measured in advance. The calibration data is then used in correction of measurements as described in more detail below.

In operation, incident power enters the circuit at the input port 42 and is sampled by the coupler 44 connected to the detector 45, which translates the sampled power to a voltage signal. The signal measured by the detector 45 represents the forward power (or incident power).

The coupler 44 transmits the power to the three port microwave circulator 41 which transmits the power in one direction to the load 43. The load 43 may be an applicator or antenna, for example for medical applications.

As the load impedance may differ from the system impedance of 50Ω an impedance mismatch occurs resulting in a proportion of the power being reflected back towards the circulator 41. The circulator transmits this reflected power towards the reflected power termination 48 which absorbs the reflected power. The reflected power is sampled by the coupler 46 connected to the detector 47 which translates the sampled power to a voltage signal. The signal measured by the detector 47 represents the reflected power (or reverse/return power). In this arrangement a ratio between forward and reverse power can be measured that corresponds to the impedance of the load 43.

Figure 17B:
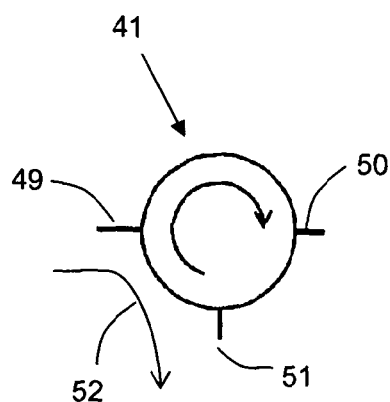
FIG. 17b is a schematic representation of a standard microwave circulator.

The microwave circulator 41 has three ports, as illustrated in FIG. 17*b*. Usually power is transferred from the first port 49 to the second port 50 and reflected power is returned from the second port 50 to the third port 51 following the direction of circulation. The circulator does possess a level of isolation between the ports (that is related to the port termination) and this can result in a small leakage signal 52 passing against the direction of circulation between adjacent ports. Ideally a microwave circulator should see a 50Ω impedance on each port to achieve optimum performance. However in medical applications the port impedance can differ significantly from 50Ω resulting in changes to the circulator performance that can include changes in isolation, changes in input match and changes in insertion loss.

Figure 17C:
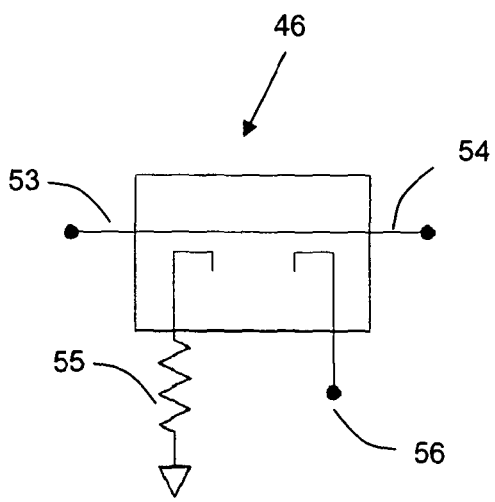
FIG. 17c is a schematic representation of a standard microwave coupler.

The microwave directional coupler 46 is a device with four ports as illustrated in FIG. 17*c*. Usually directional couplers are used to separate signals based on the direction of flow, which is from input 53 to output 54. The coupler 46 has two coupled ports, the first is the coupled output 56 and the second is the terminated port 55 (known as the isolated port) which absorbs reflected signal from the output port.

The directional coupler 46 splits a signal into two components with the coupled output 56 being attenuated for sampling purposes, this level of attenuation being the coupling factor. However as couplers are non-ideal they also allow some of signal to flow in the reverse direction. The difference between the power output at the coupled port 56 with forward power compared to reverse power is called the directivity.

Ideally a coupler should see a 50Ω impedance on each port to achieve optimum performance however in medical applications the output port impedance can differ significantly from 50Ω resulting in changes to the coupler performance that can include, changes in coupling factor, changes in match, changes in insertion loss and changes in directivity. Another coupler configuration is the dual directional coupler which is used for in line simultaneous forward and reverse power measurements. This is essentially the same as having two couplers ganged in series and being integrated into a single device with four ports and two internal isolated terminations the operation is as described previously.

Figure 18A:
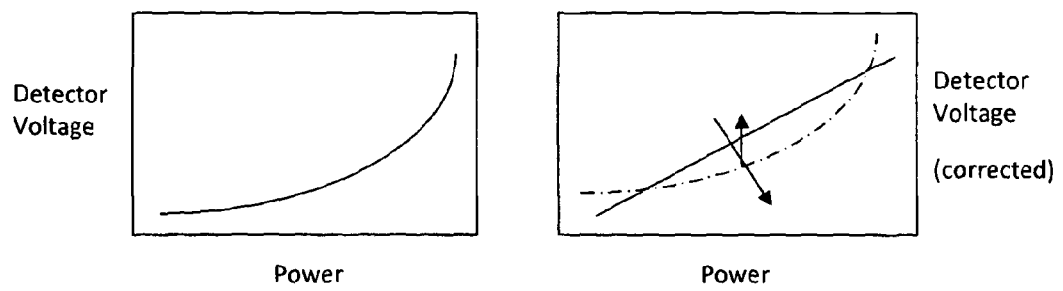
FIG. 18a is a schematic illustration of an embodiment used to linearize the detector voltage vs. power measured.

The detectors 45 and 47 possess a non linear power to voltage performance that can be linearized using a curve fitting circuit or microprocessor based lookup table to correct the value as illustrated in FIG. 18a. In this embodiment the offset and gain of an analogue circuit are compared to a measured power reference to correct the measured voltage as part of a calibration.

The coupled signal which drives the detector is affected by the load impedance presented to the system. The impedance versus coupled signal (or measured power) relationship is influenced by the entire network of impedance sensitive components including the couplers and circulator and this relationship is typically non linear. It has been found that it can be important to correct the impedance versus coupled performance in order to measure the correct power for various impedances.

In the embodiment of FIG. 17a, various known impedances are connected in place of load 73 during an initial calibration procedure and measurements are performed (for example, measurements of forward and reflected detector voltages) for each of the known impedances at different microwave input signal power levels and/or frequencies. The known impedances can be a plurality of port impedance reference standards, for example −1.5 dB, −3 dB, −6 dB −12 db, −20 dB impedances, an electrical open circuit, and an electrical short circuit.

Figure 18B:
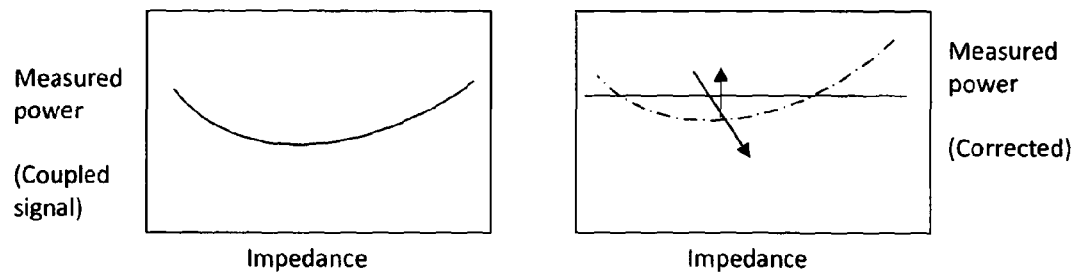
FIG. 18b is a schematic illustration of an embodiment used to linearize the measured power (from a coupler) vs. Impedance.

The performance can be linearized by the controller 40 using a curve fitting circuit or microprocessor-based lookup table to correct the value as illustrated in FIG. 18b. In this embodiment the offset and gain of an analogue circuit (FIG. 22) are compared to measured impedance references for a set power level to correct the measured signal as part of a calibration.

The measured forward to reflected power signals can be used by the controller 40 to generate a signal which is proportional to the impedance. This impedance related signal can then be used to correct the measured detector voltage for variations in output port impedance to ensure that accuracy of the measurement is not diminished should the port impedance vary.

Figure 19A:
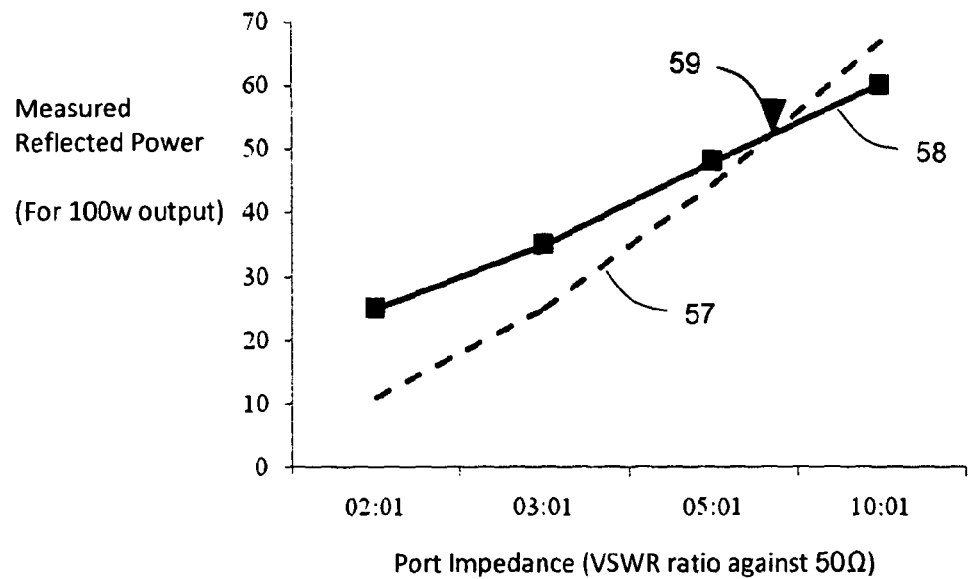
FIG. 19a is a graph of measured reflected power from a 100 W source, as a function of various port impedances compared with the theoretical measured reflected power.

Without this correction for impedance a power measurement calibrated using a specific impedance mismatch will only measure the correct power at that same single impedance point, as illustrated schematically in FIG. 19a. It can be seen in FIG. 19a that the measured power 58 agrees with the theoretical measured power 57 at one impedance point 59 and differs elsewhere due to the influence of impedance upon the measurement.

Figure 19B:
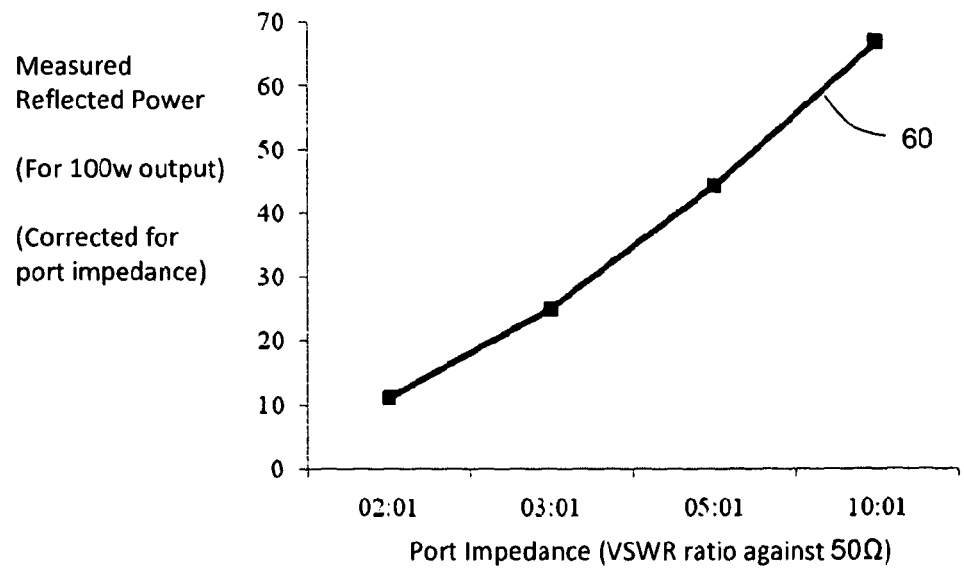
FIG. 19b is a graph of measured reflected power from a 100 W source corrected for port impedance, as a function of various port impedances.

With the measurement corrected for impedance mismatch as illustrated in FIG. 19b the corrected measured power 60 agrees with the theory 57 across all values of impedance.

Figure 20:
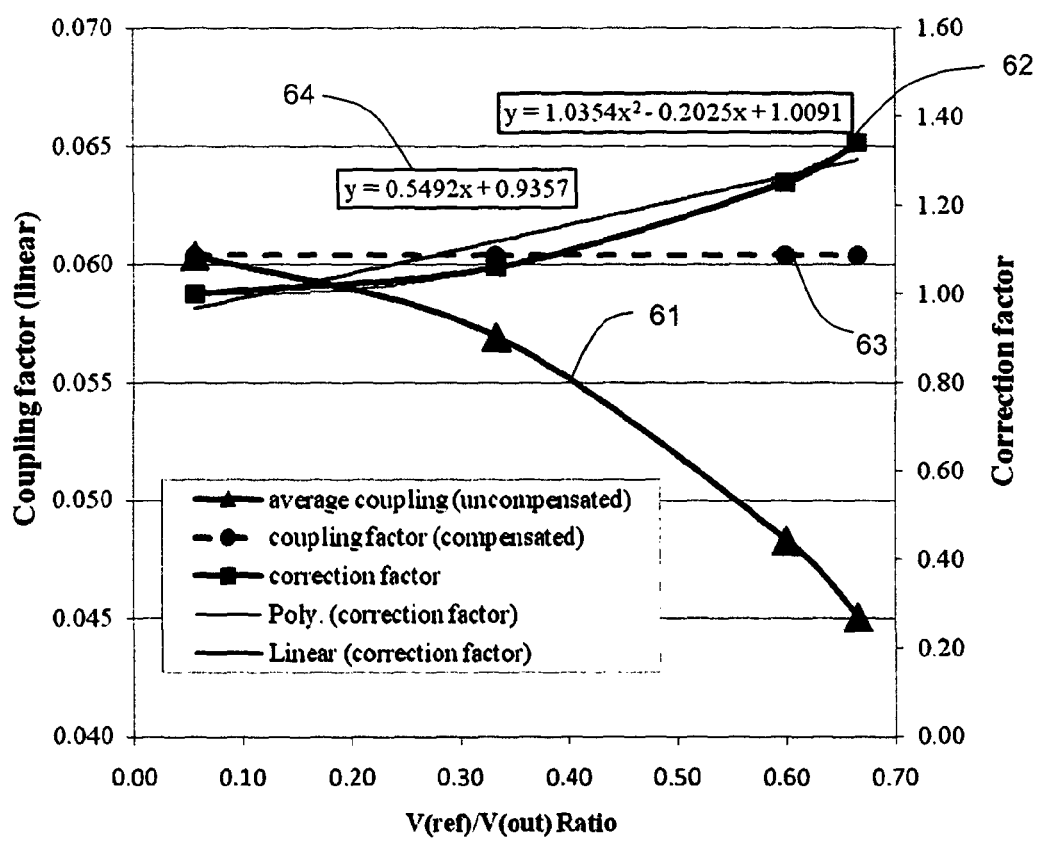
FIG. 20 is a graph of coupling factor as a function of voltage ratio and includes and illustrates the use of a linear and polynomial correction factor to stabilize the coupling factor for variations in voltage ratio.

An example of a correction is provided in FIG. 20. In FIG. 20, the coupling factor value 61 of a microwave coupler is shown to vary with increased forward to reverse power ratio. A polynomial correction factor 62 is introduced to correct the coupled value which results in the linearized (compensated) coupling factor 63 which tracks the forward to reverse power ratio. A linear correction factor 64 could also be used as an approximate means of correction. The correction factor can be generated by the controller 40 associated with the microwave source 39 using a curve fitting analogue circuit as illustrated in FIG. 22 or a microprocessor based lookup table (not shown).

Figure 21A:
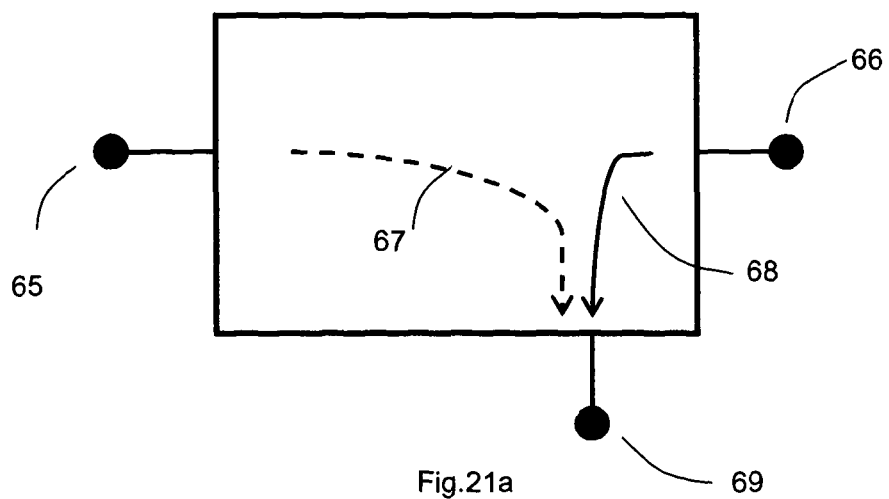
FIG. 21a is a schematic illustration of an embodiment of a microwave coupler.
Figure 21B:
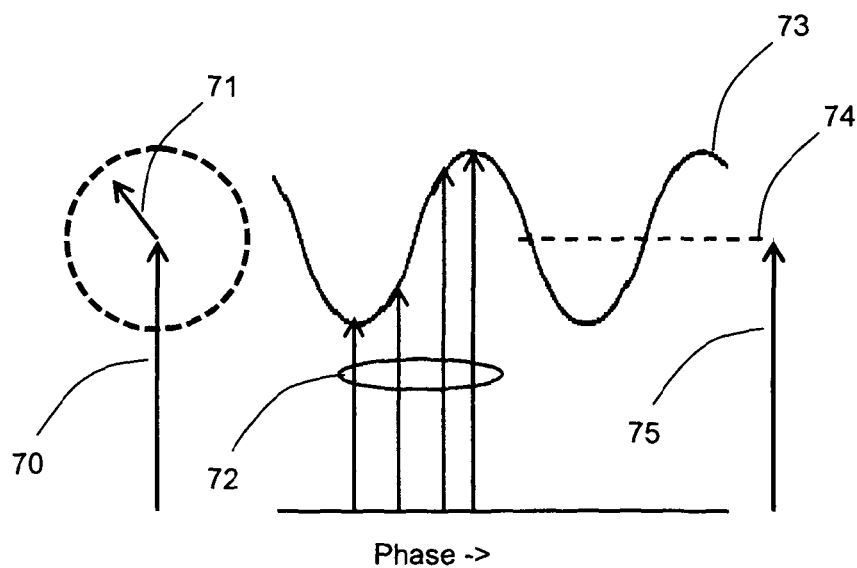
FIG. 21b is a schematic illustration of a measurement of reflected power being affected by the directivity signal in a microwave coupler and FIG. 22 is a functional representation of an analogue circuit for linearizing, curve fitting, or calibration of a measured detector signal.

A typical directional coupler is illustrated in FIG. 21a. In this schematic a reflected power signal 68 is returned from the output port 66 for a fixed impedance mismatch. A leakage signal 67 also exists as a result of the directivity and combines with the reflected power signal at the coupled port 69. As the measurement is phase/frequency sensitive the directivity signal 71 will add and cancel with the reflected signal 70 causing variations in the observed signal 72 which produces a ripple in the measurement 73. This ripple is the result of a VSWR occurring at the coupled port 69. The peak to peak value of the ripple depends upon the impedance mismatch, the directivity, the coupling factor, insertion loss and other typical system parameters for the device. When performing this measurement at a single frequency (CW), uncertainty applies; it cannot be determined if the measurement is at the minimum, the maximum, or somewhere in between. By sweeping the frequency across a range that is equivalent to 360 degrees of phase an average value for the reflected power 74 can be determined which recovers the true measurement of reflected power 75. A similar effect can be achieved for a microwave circulator as the port to port leakage acts in the same way as the directivity leakage signal.

Figure 22:
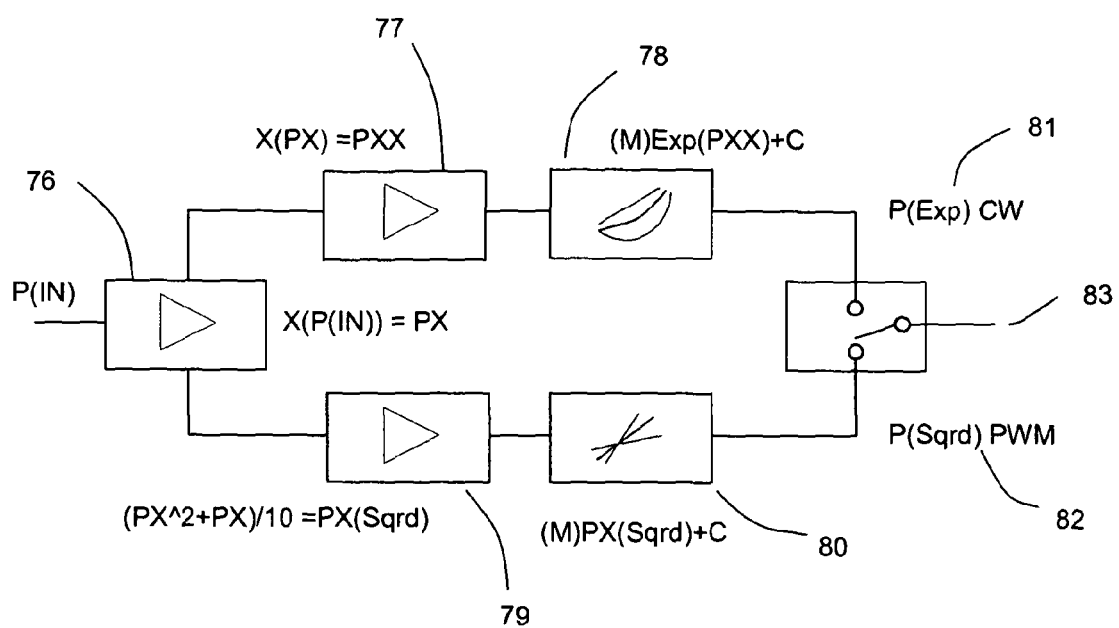

An embodiment of an analogue circuit for linearizing (curve fitting) or calibration of a measured detector signal (either forward or reflected) is illustrated in FIG. 22. In this functional schematic a measured power signal P(IN) from a detector 45 or 47 enters the circuit into an initial gain stage 76, is amplified and is then distributed to two circuits. One circuit provides an exponential to linear curve fit 77, 78 and the other provides a linear to linear curve fit, 79 80. Calibration adjustments affect the gain 77, 79 and slope 80 or exponent 78 (offset) of the circuit characteristics to linearize the output signal. The linear squared circuit corrects a PWM based linear power measurement (take from a single point on the diode power characteristic) 82 and the exponential circuit corrects a CW (continuous) measurement 81 that follows the detector diode curve characteristics for power. Either of these circuits can be selected by a switch 83 which outputs the linearized power measurement to the control system depending upon the mode of operation (internal PWM or with the amplifier 4 externally driven in CW amplifier mode).

As couplers and circulators are both phase and impedance sensitive devices, impedance mismatches coupled with phase variation in fixed frequency (CW) systems can result in very significant measurement uncertainties. The use of swept frequency sources can eliminate these uncertainties when using coupler and circulators in power measurement circuits. The measurement of reflected signals and determination of a measure of reflection have been described. It will be understood that the described embodiments can also be used to determine a measure of transmission, or a ratio of transmission to reflection.

It will be understood that the present invention has been described above purely by way of example, and modifications of detail can be made within the scope of the invention.

Each feature disclosed in the description, and (where appropriate) the claims and drawings may be provided independently or in any appropriate combination.

The invention claimed is:

1. A microwave apparatus comprising:
   a microwave source for providing a microwave signal, connectable to a load;
   a controller configured in operation to select power and a frequency range of the microwave signal to perform a desired ablation, heating or other energy delivery operation at or by the load, wherein the selected frequency range has a maximum frequency and a minimum frequency;
   wherein the microwave source provides the microwave signal of the selected power to the load and repeatedly varies an operating frequency of the microwave signal between the maximum frequency and the minimum frequency of the selected range thereby to perform the desired ablation, heating or other energy delivery operation;
   the apparatus further comprises a microwave detector for performing microwave measurements, arranged to at least one of receive reflections from or transmissions to the load in operation, wherein the microwave detector performs a plurality of measurements during the desired ablation, heating or other energy delivery operation, each measurement corresponding to a respective one of a plurality of different frequencies of the frequency range; and
   a processing device that determines from the plurality of measurements at said plurality of different frequencies at least one of a measure of reflection or a measure of transmission, wherein the processing device averages the plurality of measurements at said plurality of different frequencies such that the determined measure is representative of at least one of an average amount of reflection obtained for said plurality of different frequencies of the frequency range and an average amount of transmission obtained for said plurality of different frequencies of the frequency range during the ablation, heating or other energy delivery operation.

2. The apparatus according to claim 1, wherein the microwave source is connectable to the load via a transmission line such that in operation a voltage standing wave is formed in the transmission line by the superposition of the microwave signal provided by the source and a reflection of the microwave signal, the amplitude of the voltage standing wave (VSW) varying between a maximum and a minimum with position on the transmission line in a VSW cycle, and the frequency range is such that the varying of the frequency by the controller over the applied frequency range in operation causes amplitude of the VSW at a location of the microwave detector to vary over at least one VSW cycle.

3. The apparatus according to claim 1, wherein the microwave source is connectable to the load via a transmission line having a length L, and the frequency range has a width greater than or equal to c/2L, wherein c is the speed of light.

4. The apparatus according to claim 1, wherein the frequency range has a width greater than or equal to 50 MHz, optionally greater than or equal to 200 MHz, optionally greater than or equal to 500 MHz.

5. The apparatus according to claim 1, wherein the controller is configured to vary the frequency of the microwave signal by sweeping the frequency over the frequency range.

6. The apparatus according to claim 1, wherein the controller is configured to vary the frequency of the microwave signal over the frequency range by controlling the signal to have a sequence of different frequencies.

7. The apparatus according to claim 1, wherein the microwave signal comprises a pulsed signal and the controller is configured to vary the frequency during each pulse.

8. The apparatus according to claim 7, wherein the controller is configured to vary the frequency of the microwave signal over the applied frequency range in a repeating cycle, and the duration of each cycle is less than the duration of each pulse.

9. The apparatus according to claim 8, wherein the duration of each cycle is less than or equal to one tenth of the duration of each pulse.

10. The apparatus according to claim 1, wherein the microwave detector is configured to measure the microwave signal provided by the source and a reflection of the microwave signal, and to determine a voltage standing wave ratio (VSWR) from the measured provided signal and the measured reflection.

11. The apparatus according to claim 1, wherein the measure of the amount of reflection comprises a VSWR for the frequency range.

12. The apparatus according to claim 1, wherein the processing device is configured to compare the measure of the amount of at least one of reflection or transmission to a threshold.

13. The apparatus according to claim 12, wherein the controller is configured to vary at least one property of the microwave signal provided by the source in dependence on the comparison.

14. The apparatus according to claim 13, wherein the controller is configured to at least one of: reduce or increase the power of the microwave signal in dependence on the comparison; or to halt application of the microwave signal to the load in dependence on the comparison.

15. The apparatus according to claim 1, wherein the microwave source comprises a swept frequency oscillator and a microwave amplifier, and the controller is configured to drive the microwave amplifier in a linear region of its performance characteristic in operation.

16. The apparatus according to claim 1, wherein the microwave source comprises an external microwave oscillator, an amplifier for amplifying signals from the external microwave oscillator to provide the microwave signal, and the controller is configured to apply a control signal to the amplifier to control the microwave signal.

17. The apparatus according to claim 1, wherein the load comprises a probe or applicator, wherein the probe or the applicator is configured for applying microwave radiation to biological tissue.

18. The apparatus according to claim 1, wherein the controller is configured to control the source in operation to provide a microwave signal to perform an operation, for example an ablation operation, on biological tissue.

19. The apparatus according to claim 1, wherein the load is connected to at least one of a microwave coupler and a microwave circulator.

20. The apparatus according to claim 1, further comprising a data store for storing calibration data that relates measurement values to the value of load impedance, wherein the controller is configured to apply a correction to the measurements based upon the calibration data.

21. The apparatus according to claim 20, wherein the measurement values of the calibration data comprise at least one of transmitted signal level, reflected signal level and transmission to reflection ratio.

22. A method of monitoring at least one of reflection or transmission, comprising:
- providing a microwave signal to a load;
- repeatedly varying an operating frequency of the microwave signal over a frequency range, between a maximum frequency and a minimum frequency of the frequency range, thereby to perform a desired ablation, heating or other energy delivery operation at or by the load;
- performing a plurality of microwave measurements during the desired ablation, heating or other energy delivery operation, each at a respective one of a plurality of different frequencies of the frequency range and each comprising at least one of reflection or transmission of the microwave signal; and
- determining from the plurality of measurements at said plurality of different frequencies a measure of at least one of reflection or transmission, wherein the determining comprises averaging the plurality of measurements at said plurality of different frequencies such that the determined measure is representative of at least one of an average amount of reflection and an average amount of transmission obtained for said plurality of different frequencies of the frequency range during the ablation, heating or other energy delivery operation.

23. An article of manufacture including a non-transitory, tangible computer readable storage medium having instructions stored thereon that, in response to execution by a computer-based system configured for monitoring microwave at least one of reflected or transmission, cause the computer-based system to perform operations comprising:
- providing, by the computer-based system, a microwave signal to a load;
- repeatedly varying, by the computer-based system, an operating frequency of the microwave signal over a frequency range, between a maximum frequency and a minimum frequency of the frequency range, thereby to perform a desired ablation, heating or other energy delivery operation at or by the load;
- performing, by the computer-based system, a plurality of microwave measurements during the desired ablation, heating or other energy delivery operation, each at a respective one of a plurality of different frequencies of the frequency range and each comprising at least one of reflection and transmission of the microwave signal; and
- determining, by the computer-based system, from the plurality of measurements at said plurality of different frequencies a measure of at least one of reflection and transmission, wherein the determining comprises averaging the plurality of measurements at said plurality of different frequencies such that the determined measure is representative of at least one of an average amount of reflection and an average amount of transmission obtained for said plurality of different frequencies of the frequency range during the ablation, heating or other energy delivery operation.

24. A microwave apparatus comprising:
- a microwave source for providing a microwave signal, connectable to a load;
- control means configured in operation to select power and a frequency range of the microwave signal to perform a desired ablation, heating or other energy delivery operation at or by the load, wherein the selected frequency range has a maximum frequency and a minimum frequency;
- wherein the microwave source provides the microwave signal of the selected power to the load and repeatedly varies an operating frequency of the microwave signal between the maximum frequency and the minimum frequency of the selected range thereby to perform the desired ablation, heating or other energy delivery operation;
- the apparatus further comprises a microwave detector for performing microwave measurements, arranged to at least one of receive reflections from or transmissions to the load in operation, wherein the microwave detector performs a plurality of measurements during the desired ablation, heating or other energy delivery operation, each measurement corresponding to a respective one of a plurality of different frequencies of the frequency range; and
- means for determining from the plurality of measurements at said plurality of different frequencies at least one of a measure of reflection or a measure of transmission, wherein the means for determining averages the plurality of measurements at said plurality of different frequencies such that the determined measure is representative of at least one of an average amount of reflection obtained for said plurality of different frequencies of the frequency range and an average amount of transmission obtained for said plurality of different frequencies of the frequency range during the ablation, heating or other energy delivery operation.

\* \* \* \* \*

UNITED STATES PATENT AND TRADEMARK OFFICE
CERTIFICATE OF CORRECTION

PATENT NO. : 9,007,070 B2
APPLICATION NO. : 13/509835
DATED : April 14, 2015
INVENTOR(S) : Eamon Mcerlean et al.

It is certified that error appears in the above-identified patent and that said Letters Patent is hereby corrected as shown below:

Claims

In Column 21 Line 50, Claim 2, after "causes" please insert --the--.

In Column 22 Lines 4-5, Claim 8, please delete "thecontroller" and insert therefor --the controller--.

In Column 22 Line 56, Claim 19, please delete "and" and insert therefor --or--.

In Column 22 Line 66, Claim 21, please delete "and" and insert therefor --or--.

Signed and Sealed this
Ninth Day of February, 2016

Michelle K. Lee
*Director of the United States Patent and Trademark Office*